United States Patent [19]

Saucy et al.

[11] 3,984,428
[45] Oct. 5, 1976

[54] ISOXAZOLYL-SUBSTITUTED PERHYDROBENZINDENES

[75] Inventors: Gabriel Saucy, Essex Falls; John William Scott, Upper Montclair, both of N.J.

[73] Assignee: Hoffmann-La Roche Inc., Nutley, N.J.

[22] Filed: May 21, 1974

[21] Appl. No.: 472,033

Related U.S. Application Data

[60] Division of Ser. No. 278,889, Aug. 9, 1972, abandoned, which is a division of Ser. No. 39,560, May 21, 1970, Pat. No. 3,691,190, which is a continuation-in-part of Ser. No. 778,314, Nov. 22, 1968, Pat. No. 3,700,661.

[52] U.S. Cl. .................................................. 260/307 H
[51] Int. Cl.² ............................................ C07D 261/08

[58] Field of Search ................................ 260/307 H

[56] References Cited
UNITED STATES PATENTS

| | | | |
|---|---|---|---|
| 3,691,190 | 9/1972 | Saucy et al. | 260/307 H |
| 3,700,661 | 10/1972 | Saucy et al. | 260/240 E |

*Primary Examiner*—Raymond V. Rush
*Attorney, Agent, or Firm*—Samuel L. Welt; George M. Gould; Raymond R. Wittekind

[57] ABSTRACT

6[(4-Isoxazolyl)-methyl]perhydro-1H-benz[e]indenes, useful for the preparation of pharmaceutically valuable 19-norsteroids and estranes by degradation of the isoxazolylmethylene moiety followed by cyclization, is disclosed.

6 Claims, No Drawings

ISOXAZOLYL-SUBSTITUTED PERHYDROBENZINDENES

CROSS-REFERENCE TO RELATED APPLICATIONS

This application is a divisional of Ser. No. 278,889, filed Aug. 9, 1972, now abandoned, which in turn is a divisional of Ser. No, 39,560, now U.S. Pat. No. 3,691,190, which in turn is a continuation-in-part of Ser. No. 778,314, now U.S. Pat. No. 3,700,661.

BACKGROUND OF THE INVENTION

In recent years, much effort has been devoted to the total synthesis of steroids. The medicinally important 19-norsteroids have been the subject of a large number of chemical investigations, cf. D. Djerassi, Science, 151, 1055 (1966); L. Velluz et al., Tetrahedron Supplement 8, Part II, 495 (1966). 19-Norsteroids have been prepared in accordance with prior art teachings by the reduction of Ring A aromatic steroids either chemically [A. L. Wilds et al., J. Am. Chem. Soc. 75, 5366 (1953)] or photolytically [J. A. Waters et al., J. Am. Chem. Soc. 89, 1022 (1967)]. Other methods known in the art for the preparation of 19-norsteroids include oxidation of the C-19 methyl group of a steroid to the corresponding carboxylic acid followed by acidic decarboxylation of the resulting 19-carboxy-$\Delta^4$-3-keto system. [A. Bowers et al., J. Am. Chem. Soc. 84, 3204 (1962)].

The present invention relates to certain polycyclic compounds and processes for their synthesis. The novel intermediates and processes of this invention provide a new synthetic route for the preparation of pharmaceutically valuable 19-nor-steroids. Further, the intermediates and processes of the invention provide a novel route for the preparation of pharmaceutically valuable estrones. In synthesis of steroidal materials, steric considerations are of great significance. The most used steroidal compounds are those having a C/D-trans-ring junction with the substituent in the 13-position being in the β-configuration. The present invention provides a facile total synthesis of 13β-C/D-trans-steroidal materials. This desirable result is obtained via a unique asymmetric induction followed by subsequent stereospecific reaction steps.

SUMMARY OF THE INVENTION

A 3,5-disubstituted-4-isoxazolylmethylene group is employed as a precursor of the steroidal Ring A in this synthesis. The novel use of this group as a precursor of the steroidal Ring A provides an improved method for obtaining extremely high yields of optically active pharmaceutically valuable steroid end-products. This is in part due to the chemically stable nature of the isoxazole group to the acids, bases, hydrogenations and other process perameters employed throughout the synthesis. By-product formation has been substantially reduced by the processes of this invention, thereby facilitating costly separating and purifying procedures. The substantial elimination of by-product formation also contributes to the obtention of the high end-product yields. Further, it has been found that by means of the resolutions of starting materials and subsequent stereospecific reaction steps of the processes of this invention, the direct obtention of optically active end-products is greatly facilitated.

In one aspect, this invention relates to substituted-isoxazole starting materials of formulae II-a and II-b, intermediates therefor and their method of preparation via a Wittig-type reaction of a phosphonium ylid of formula D and acrolein dimer (formula E) in accordance with Reaction Schemes A and B.

In Reaction Schemes A and B, $R_{15}$ is selected from the group consisting of lower alkyl and hydrogen; $R_{16}$ is selected from the group consisting of lower alkyl, lower alkylaryl, aralkyl and hydrogen; $X'$ is an inorganic anion derived from a mineral acid; $R'_1$, $R'_2$ and $R'_3$ are independently selected from the group consisting of lower alkyl phenyl and phenyl-lower alkyl; $R_{17}$ is selected from the group consisting of mono-hydrocarbylamino and di-hydrocarbylamino and acid salts thereof; $R_{10}$ is lower alkyl; $R_4$ is selected from the formulae $R'_aNH$ and $R'_aO$ wherein $R'_a$ is an optically active hydrocarbyl residue.

Reaction Scheme A

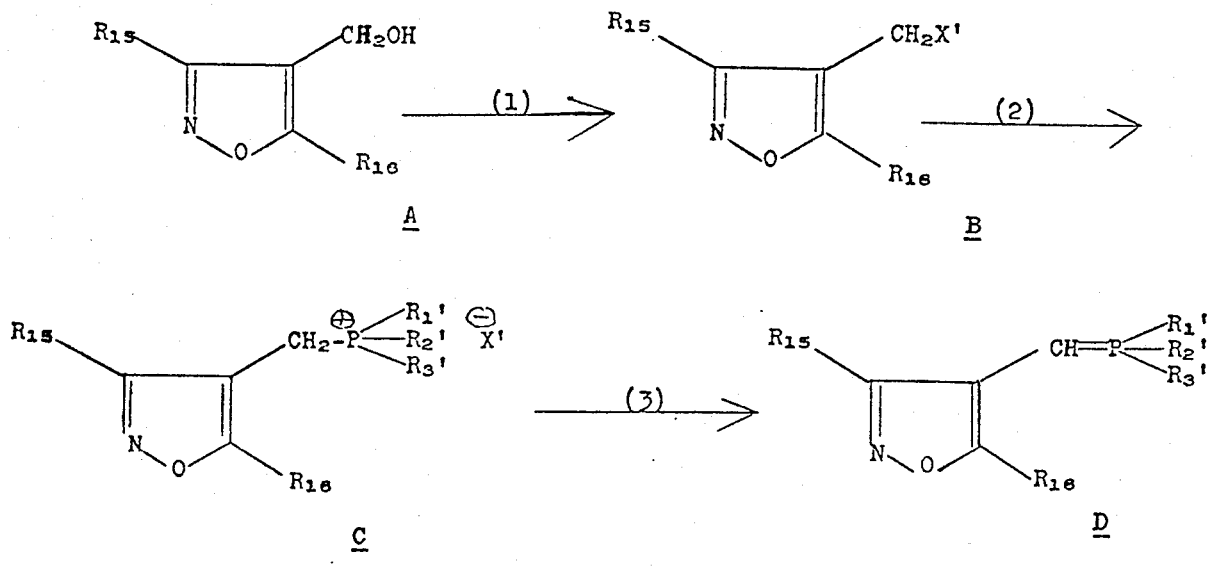

wherein $R_{15}$, $R_{10}$, $X'$, $R_1'$, $R_2'$, and $R_3'$ are defined as aforesaid

Reaction Scheme B

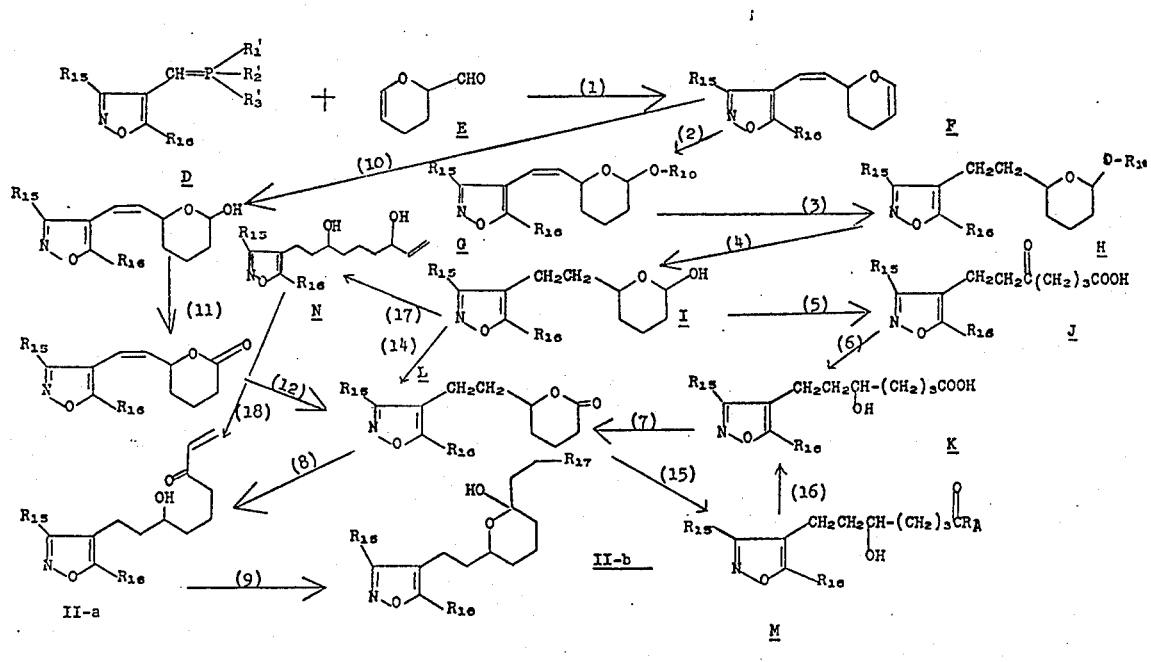

wherein $R_A$, $R_{10}$, $R_{15}$, $R_{10}$, $R_1'$, $R_2'$, $R_3'$ and $R_{17}$ are defined as aforesaid.

In another aspect, this invention is directed to the process and compounds represented schematically in Reaction Scheme C. Thus, the 3-substituted-6aβ-alkyl-cyclopenta[f][1]-benzopyrans or naptho[2,1-b]pyrans of formula I-a are prepared by reacting a 9-(3,5-substituted-4-isoxazolyl)-7-hydroxy-1-nonen-3-one of the formula II-a or a tetrahydropyran-2-ol variant thereof of the formula II-b with a 2-lower alkyl cycloalkane-1,3-dione of the formula III. The 3aβ-alkyl-7-oxo-1H-benz[e]indenes and 8aβ-alkyl-3H-phenanthren-2-ones of the formula XI are prepared by cyclizing the 4- or 5-(3-oxo-alkyl)-perhydroindene-5-ones and perhydronaphthalene-6-ones of formula X which are obtained by oxidizing the pyrans of formula I-c. The latter perhydropyran intermediates are prepared by saturating the double bond of the diene of formula I-a and introducing $R_2O$ (defined below) at the 4a-position and a hydrogen atom at the 9b- or 10a-position of monoene 1-b.

Alternatively, the compounds of formula XI are prepared by alkylation (not shown in Reaction Scheme C) of a 3aβ-alkyl-7-oxo-7H-benz[e]indene or 8aβ-alkyl-3H-phenanthren-2-one with a 3,5-disubstituted-4-halomethyl isoxazole.

In Reaction Scheme C, Y is a substituted isoxazole of the formula

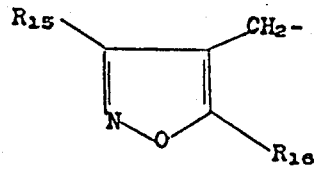

wherein $R_{17}$, $R_{15}$ and $R_{10}$ are defined as aforesaid; $R_1$ is a primary alkyl group of from 1 to 5 carbon atoms; $R_2$ is selected from the group consisting of hydrogen, lower primary alkyl or lower acyl; Z is selected from the group consisting of carbonyl, lower alkylenedioxymethylene, di-lower alkoxy-methylene, phendioxymethylene and a group of the formula

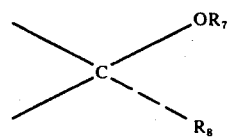

wherein $R_7$ is selected from the group consisting of hydrogen, lower alkyl, lower alkoxy-lower alkyl, phenyl-lower alkyl, tetrahydropyranyl and lower acyl; $R_3$ is selected from the group consisting of hydrogen and lower aliphatic hydrocarbyl; and m is an integer having a value from 1 to 2.

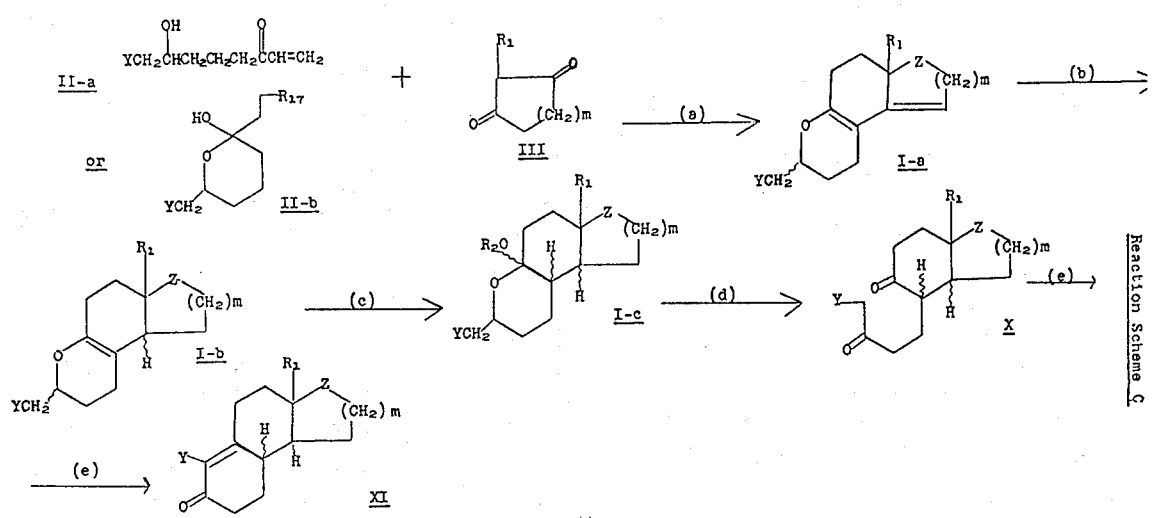

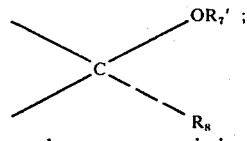

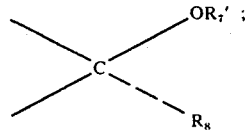

wherein Y, $R_{17}$, $R_1$, $R_2$, Z and m are as defined aforesaid.

A still further aspect of this invention relates to the process and intermediate compounds employed to convert the benz[e]indenes and phenanthren-2-ones of formula XI in accordance with Reaction Schemes D and D' to 19-nor-steroids of the formula XIV-a, wherein $R_{15}$, $R_{16}$, $R_1$, Z and m are as defined as aforesaid and X is selected from the group consisting of lower alkylenedioxy-methylene, phendioxy-methylene, di-lower alkoxy-methylene, the monothia, monoaza or dithia chalcogen thereof and a group of the formula

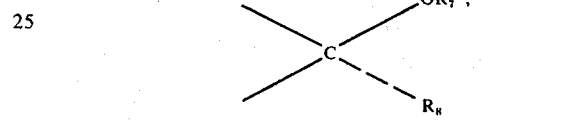

$R'_{15}$ is selected from the group consisting of hydrogen and lower alkyl; Z' is selected from the group consisting of carbonyl and a group of the formula

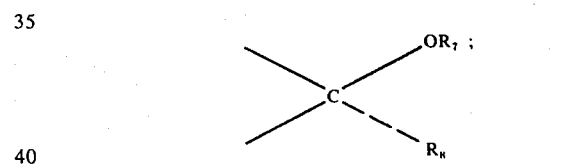

W is selected from the group consisting of carbonyl and a group of the formula $$\diagup\!\!\!\!\diagdown C \diagdown\!\!\!\!\diagup \begin{array}{l} OR_7 \\ R_8 \end{array} ;$$

Z'' is selected from the group consisting of lower alkylenedioxy-methylene, phendioxy-methylene, di-lower alkoxy-methylene, the monothia, monoaza or dithia chalcogen thereof and a group of the formula $$\diagup\!\!\!\!\diagdown C \diagdown\!\!\!\!\diagup \begin{array}{l} OR_7 \\ R_8 \end{array} ;$$

$R_7$ and $R_8$ are defined as aforesaid and $R_7'$ is selected from the group consisting of hydrogen, lower alkyl, lower alkoxy-lower alkyl, phenyl-lower alkyl and tetrahydropyranyl.

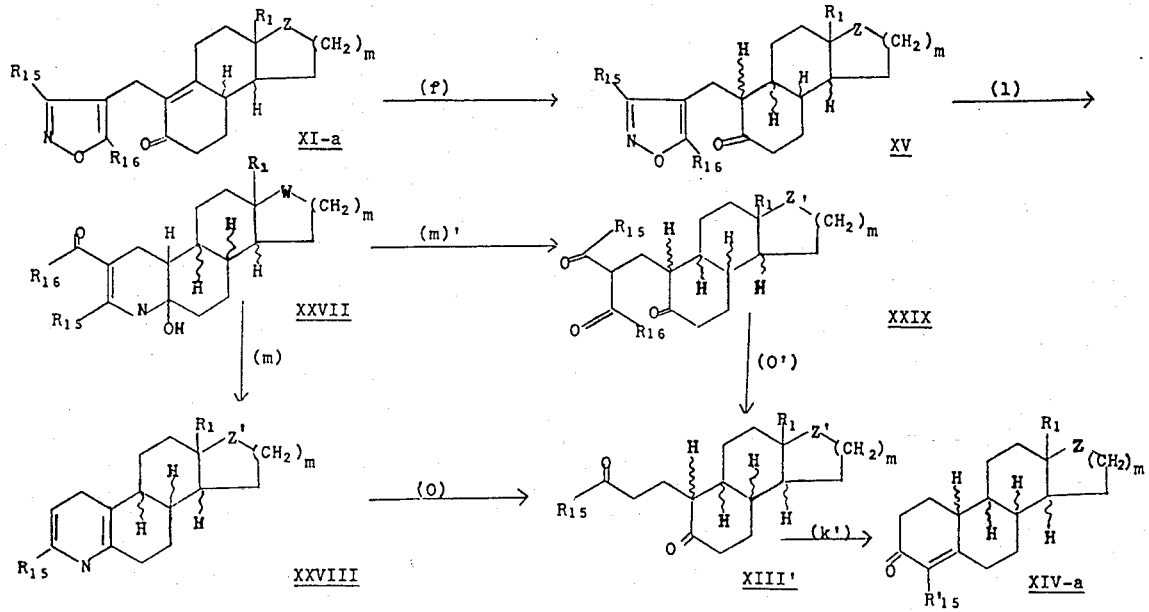

wherein W, $R_1$, $R_{15}$, $R_{16}$, Z, Z', $R'_{15}$ and m are defined aforesaid denes and phenanthren-2-ones of the formula XI-a, in accordance with Reaction Scheme E, to the dienones

REACTION SCHEME D'

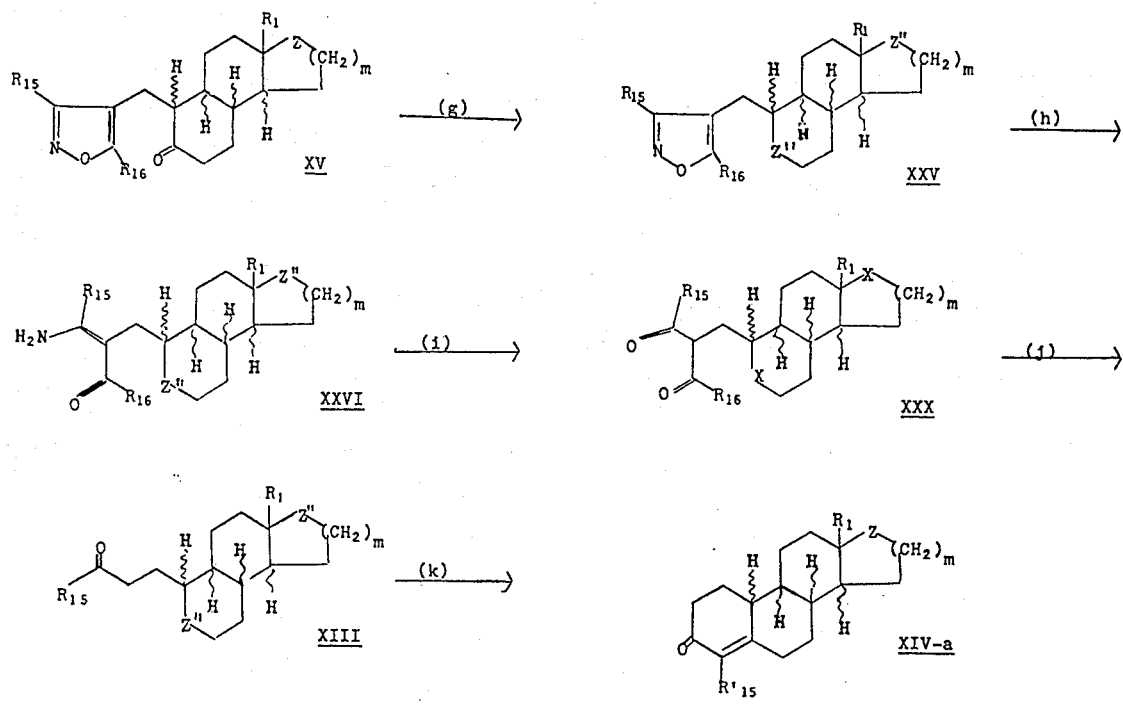

wherein X, $R_1$, $R_{15}$, $R_{16}$, Z, Z'', $R'_{15}$ and m are defined aforesaid Yet another aspect of this invention relates to the conversion of, via novel intermediates, the benz[e]inof formula XXXV wherein $R_{15}$, $R'_{15}$, W, X, $R_{16}$, Z, Z'' and m are as defined aforesaid and V is selected from the group consisting of lower alkylenedioxy-methylene, di-lower alkoxy-methylene and phendioxy-methylene.

REACTION SCHEME E

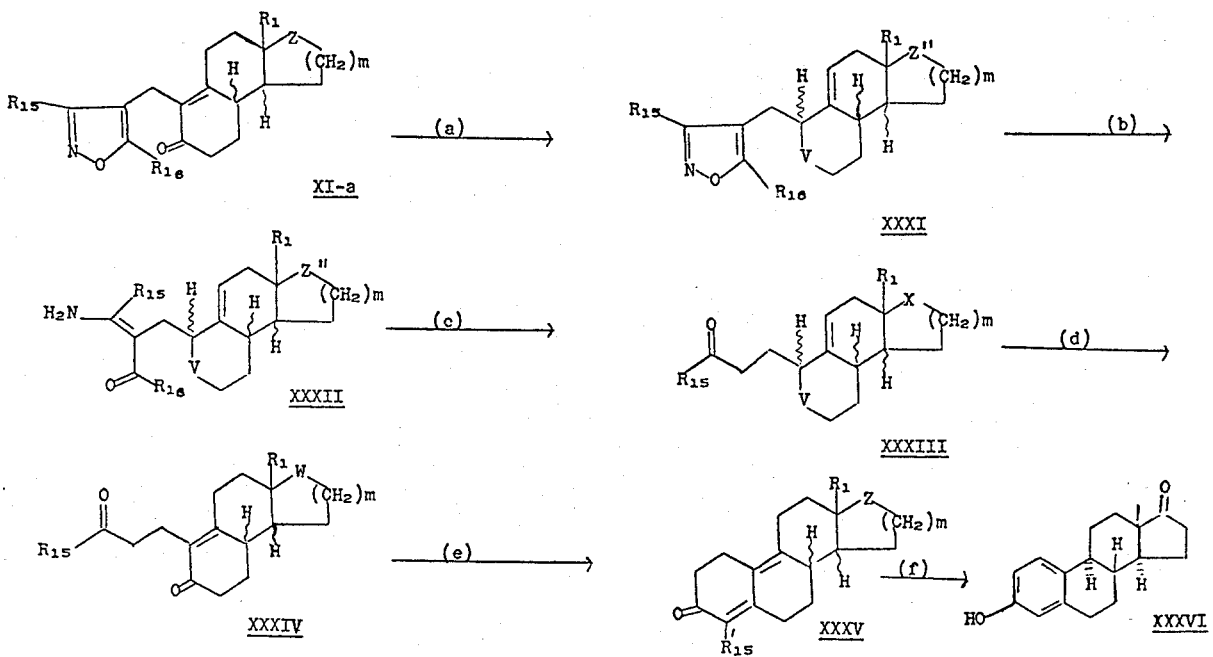

wherein R'$_{15}$, W, Z'', R$_1$, R$_{15}$, X, V, and m are defined as aforesaid.

DETAILED DESCRIPTION OF THE INVENTION

As used throughout the specification and appended claims, the term "hydrocarbyl group" denotes a monovalent substituent consisting solely of carbon and hydrogen; the term "hydrocarbylene" denotes a divalent substituent consisting solely of carbon and hydrogen and having its valence bonds from different carbons; the term "aliphatic", with reference to hydrocarbyl or hydrocarbylene groups, denotes groups containing no aromatic unsaturation, but which can be otherwise saturated or unsaturated, i.e., an alkyl or alkylene, or an aliphatic group containing olefinic or acetylenic unsaturation; the term "alkyl group" denotes a saturated hydrocarbyl group, whether straight or branched chain; the term "primary alkyl group" denotes an alkyl group having its valence bond from a carbon bonded to at least two hydrogens; the term "acyl group" denotes a group consisting of the residue of a hydrocarbyl monocarboxylic acid formed by removal of the hydroxyl portion of the carboxyl group; the term "oxyhydrocarbyl" denotes a monovalent saturated cyclic or acyclic group consisting of carbon, hydrogen, and oxygen containing only one oxygen in the form of an ether linkage and includes tetrahydropyranyloxy, and other alternate expressions such as lower alkoxy and lower alkoxy-lower alkyl; and the term "lower", as applied to any of the foregoing groups, denotes a group having a carbon skeleton containing up to and including eight carbons, such as methyl, ethyl, butyl, tert.-butyl, hexyl, 2-ethylhexyl, vinyl, butenyl, hexenyl, ethinyl, ethylene, methylene, formyl, acetyl, 2-phenylethyl, benzoyl, methoxymethyl, 1-methoxyethyl, tetrahydropyran-2-yl and the like. The phraseology "lower alkylenedioxy, the monothia, monoaza or dithia chalcogen thereof" is used to indicate a ketalized oxo or thio moiety and comprehends moieties of the formula —OR$_8$O—, —OR$_8$S—, —OR$_9$N— or —SR$_9$S— wherein R$_9$ is lower alkylene. Exemplary moieties are 1,2-ethylenedioxy, 2,2-dimethyl-1,3-propylenedioxy, 1,2-ethylenedimercapto, 2,3-butylenedioxy and the like. Phendioxy denotes a dihydroxy aryl group such as catechol formed by removal of the hydrogen atoms from both hydroxyl groups. By the terms alkoxy and alkoxy-lower alkyl are meant alkyl and alkyloxy-lower alkyl groups such as methoxy, ethoxy, tertiary-butoxy, 1-methoxy-ethyl, 2-ethoxy-ethyl and the like. The phraseology "lower aralkyl" denotes groups such as benzyl, 1-phenylethyl, 4-phenylbutyl and the like. The term "lower alkylaryl" comprehends ethylphenyl, o-tolyl and the like. Halogen denotes all halogens, e.g., chlorine, fluorine, iodine and bromine.

In the formulae presented herein, the various substituents on cyclic compounds are joined to the cyclic nucleus by one of three notations, a solid line (—) indicating a substituent which is in the β-orientation (i.e., above the plane of the paper), a dotted line (----------) indicating a substituent which is in the α-orientation (below the plane of the paper), or a wavy line (∼∼∼) indicating a substituent which may be in either the α-or β-orientation. The formulae represented in Reaction Schemes C, D, D' and E indicate the compounds in their racemic form except for the substituent defined by R$_1$ which has been arbitrarily indicated as having the β-orientation. However, it will be appreciated that the synthesis described herein uniquely lends itself to the preparation of each of the compounds represented in the above-mentioned reaction schemes in its optically active form, in which case the indicated absolute configuration at C$_{13}$ (steroid numbering) is that of naturally occuring steroids. The R and S designation of absolute stereochemistry employed herein is fully described in R. S. Cahn at al., Experientia 12, 81 (1956).

In one aspect, this invention relates to the novel starting materials of the formulae II-a and II-b, intermediates therefor and their method of preparation schematically represented by Reaction Schemes A and B.

Illustrative examples of the substituted isoxazoles of formulae II-a and II-b include: 9-(3,5-dimethyl-4-isoxazolyl)-7-hydroxy-1-nonen-3-one; 9-(3-methyl-4-isoxazolyl)-7-hydroxy-1-nonen-3-one; 9-(3,5-diethyl-4-isoxazolyl)-7-hydroxy-1-nonen-3-one; 9-(5-ethyl-4-isoxazolyl)-7-hydroxy-1-nonen-3-one; 9-(3-methyl-5-phenyl-4-isoxazolyl)-7-hydroxy-1-nonen-3-one; 2-(2-diethylaminoethyl)-6-[2-(3,5-dimethyl-4-isoxazolyl)ethyl]-tetrahydropyran-2-ol; 2-(2-dimethylaminoethyl)-6-[2-(3-ethyl-4-isoxazolyl)ethyl]-tetrahydropyran-2-ol and the like.

Other novel intermediates prepared in Reaction Scheme B are of the formula:

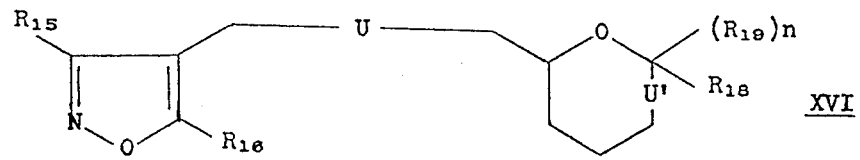

wherein R$_{18}$ when taken alone is hydrogen; (R$_{19}$) n when taken alone is lower alkoxy, lower acyloxy or hydroxy; and R$_{18}$ and (R$_{19}$) n when taken together are carbonyl; U and U' are independently a single or a double bond; R$_{15}$ and R$_{16}$ are defined as aforesaid; n is an integer having a value of from 0 to 1 and is 0 when U' is a double bond.

Subgeneric to the compounds of formula XVI are novel compounds of the formula:

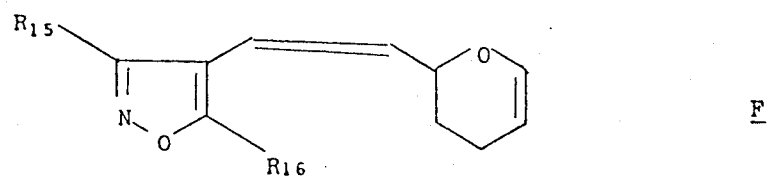

F

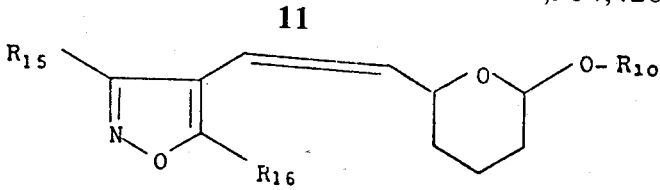

G

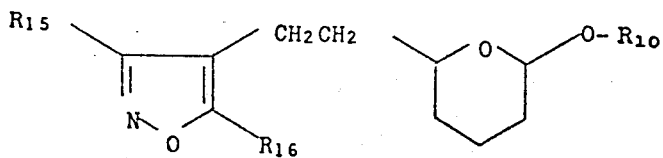

H

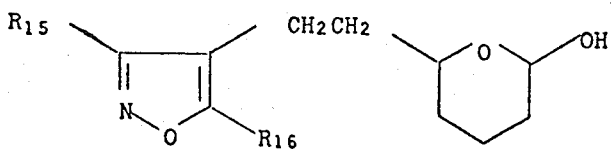

I

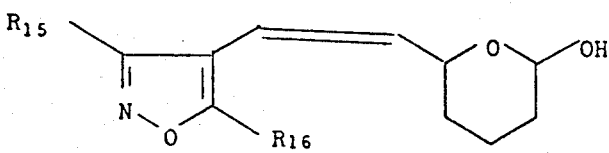

O

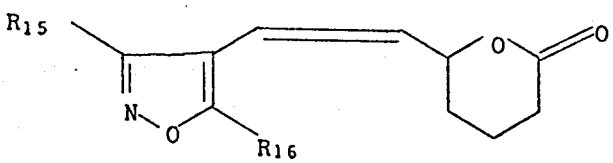

P

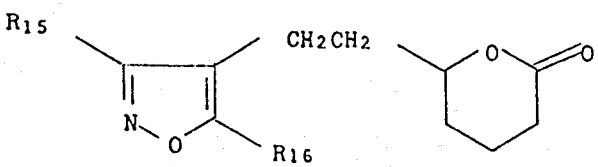

L wherein $R_{15}$, $R_{16}$, and $R_{10}$ are defined as aforesaid.

The 9-(3,5-disubstituted-4-isoxazolyl)-7-hydroxy-1-nonen-3-ones of formula II-a and 2-(2-hydrocarbylaminoethyl)-6-[2-(3,5-disubstituted-4-isoxazolyl)ethyl]-tetrahydropyran-2-ols of formulae II-b can be obtained in accordance with Reaction Schemes A and B via a Wittig-type reaction of acrolein dimer and a novel compound of the formula

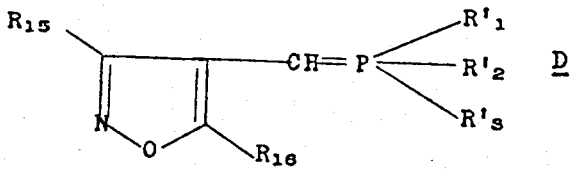

D wherein $R'_1$, $R'_2$, $R'_3$, $R_{15}$ and $R_{16}$ are defined as aforesaid.

Preferred compounds of formula D are those wherein $R'_1$, $R'_2$ and $R'_3$ are each phenyl.

Substituted hydroxy isoxazole compounds of formula A of Reaction Scheme A can be conveniently obtained by means known in the art from the corresponding 3,5-disubstituted-4-carboxy-isoxazoles. [Cf., G. Stork et al., J. Am. Chem. Soc. 89, 5461 (1967)].

The alcohols of formula A are converted to the compounds of formula B, in accordance with Step (1) of Reaction Scheme A. Suitably, the anion represented by X' is an inorganic anion derived from a mineral acid e.g., chloride, bromide, iodide, sulfate or the like. A preferred anion is chloride in which case the compounds of formula B can be obtained by the reaction of the alcohols of formula A with, for example, thionyl chloride in methylene chloride solvent at a temperature of approximately −10°C. to +30°C.

The phosphonium salts of formula C can be obtained in accordance with Step (2) of Reaction Scheme A by treatment of the halide B with the desired phosphine reagent such as, for example, triethylphosphine, triphenylphosphine, bis-(diethyl)-phenylphosphine and the like in a suitable solvent preferably a hydrocarbon, e.g., benzene, toluene or the like at the reflux temperature of the solvent. The reaction is preferably conducted under a nitrogen atmosphere.

The ylids of formula D can be generated from the compounds of formula C in accordance with Step (3)

of Reaction Scheme A by treatment of the compounds of the formula C with an acid binding agent such as for example, with an alkali metal-lower alkoxide, for example, sodium methoxide; an alkali metal hydroxide such as sodium hydroxide; or an alkali metal hydride such as sodium hydride in a suitable solvent, preferably dimethylsulfoxide. [Cf. R. Greenwald et al., J. Org. Chem. 28, 1128 (1963)].

The thus obtained Wittig reagent of formula D can be employed to prepare the vinyl pyran compounds of formula F as schematically represented in Reaction Scheme B by reacting the compounds of formula D with acrolein dimer. The reaction is suitably conducted at a temperature between room temperature and 150°C. It has been found that a preferable temperature range in which to conduct the reaction is between 65° and about 75°. The quantity of reactants used is not critical and an excess of either can be used. However, it has been found advantageous to use an essentially equimolar ratio of reactants. This reaction is suitably effected in a solvent such as, for example, ethers, e.g., lower alkyl ethers such as dioxane and tetrahydrofuran; aromatic hydrocarbons such as benzene and xylene; di-lower alkyl-lower alkanoylamides such as dimethylformamide and dimethylacetamide; and dimethylsulfoxide. A preferred solvent for this reaction is dimethylsulfoxide. Alternatively, the phosphonium salts of formula C can be reacted directly with acrolein dimer by generating in situ the ylid of formula D by adding the acid binding agent to the reaction system.

Conversion of the Wittig adduct of formula F to the heptanoic acid lactones of formula L can be accomplished via three separate reaction schemes as exemplified in Reaction Scheme B.

Thus, one method for preparing the lactones of formula L in accordance with Steps (10), (11) and (12) of Reaction Scheme B comprises hydrating the vinyl pyrans of formula F to the hemiacetals of formula O in accordance with Step (10). The hydration is suitably effected at room temperature in an inert organic solvent such as tetrahydrofuran, dioxane, or a di-lower alkyl ketone such as acetone by means of a mineral acid, preferably hydrochloric acid or sulfuric acid. The hemiacetals of formula O can be converted to the vinyl lactones of formula P in accordance with process step (11) by oxidizing with a suitable oxidizing agent, preferably manganese dioxide in a hydrocarbon solvent, preferably benzene at room temperature.

The heptanoic acid lactones of formula L are obtained in accordance with Step (12) of Reaction Scheme B by selective hydrogenation of the heptenoic acid lactones of formula P. A significant aspect of the instant synthesis lies in the selective hydrogenation of olefinically unsaturated compounds containing an isoxazole moiety, e.g., Step (12) of Reaction Scheme B, without substantially attacking the isoxazole group. It is essential that this hydrogenation reaction be conducted so as to avoid any significant hydrogenation of the isoxazole moiety. The hydrogenation is thus suitably conducted in the presence of a noble metal catalyst, such as palladium, platinum, rhodium, etc. under mild reaction conditions, viz., without the addition of heat and substantially at atmospheric pressure. The noble metal catalyst can be utilized with or without a carrier and if a carrier is used, conventional carriers are suitable. It is preferred to use a catalyst comprising palladium on a carbon carrier. The ratio of catalyst to substrate is not critical and can be varied. However, it has been found advantageous to use a weight ratio of catalyst to substrate from about 1:5 to about 1:100. Especially preferred is a ratio of 1:25. The hydrogenation is suitably effected in the presence of an inert organic solvent, optionally in the presence of acids or mono, di or trialkyl amines. Suitable solvents which may be employed are ethers, such as diethylether or tetrahydrofuran; lower alkyl esters of lower alkanoic acids such as ethyl acetate; and aromatic hydrocarbons such as toluene or benzene and the like. It is especially preferred to conduct the hydrogenation using an ethyl acetate solvent.

Alternatively, lactones of the formula L may be prepared from the vinyl pyrans of formula F as exemplified in Reaction Scheme B by first preparing the hemiacetals of formula I via process Steps (2), (3) and (4). Thus, in accordance with Step (2), the vinyl pyran isoxazoles of formula F are converted to the acetals of formula G by an alcohol addition process. The conversion is suitably effected using a mineral acid, preferably sulfuric acid, in the presence of a lower alcohol, preferably ethanol, which serves both as a solvent and a source for the alkoxy protecting group.

The hemiacetals of formula I can be prepared from the acetals of formula G in accordance with process steps (3) and (4) by first selectively hydrogenating the acetals of formula G employing similar hydrogenating conditions to that which were used to effect the hydrogenation of the compounds of formula P to the compounds of formula L as described above and subsequently removing the alkoxy protecting group by means of aqueous mineral acid, preferably sulfuric acid in an inert organic solvent, preferably an ether such as dioxane and tetrahydrofuran, or a di-lower alkyl ketone such as acetone. This latter reaction can be conveniently carried out at room temperature.

The lactones of formula L can be obtained from the hemiacetals of formula I via Step (14) or alternatively via the sequential Steps (5), (6) and (7) of Reaction Scheme B. Thus, the 6-hydroxy tetrahydropyranyl isoxazoles of formula I can be converted in accordance with Step (14) to the lactones of formula L if mild oxidation conditions are employed. The oxidation is suitably effected with an oxidizing agent such as manganese dioxide, nickel dioxide or the like. The reaction can be carried out in an inert organic solvent such as benzene, xylene or methylene chloride at room temperature.

Alternatively, in accordance with Steps (5), (6) and (7) of Reaction Scheme B, the lactones of formula L are prepared by first oxidizing the hemiacetals of formula I to the keto acids of formula J [Step (5)] using a strong agent, preferably Jones reagent (chromium trioxide and aqueous sulfuric acid) in the presence of an organic solvent such as lower alkyl ketones, e.g., acetone or methylethyl ketone. Selective reduction of the keto acids of formula J in accordance with Step (6) of Reaction Scheme B using a reducing agent such as sodium borohydride or lithium aluminum tri-tertiarybutoxy hydride in a suitable solvent such as, for example, ethers, e.g., tetrahydrofuran or dioxane or lower alkanols, e.g., methanol, ethanol or isopropanol, yields the hydroxy acids of formula K which on heating, preferably under reduced pressure, afford the lactones of formula L in accordance with Step (7) of Reaction Scheme B.

In accordance with Step (8) of Reaction Scheme B, the lactones of formula L can be converted to the substituted hydroxy-non-1-en-3-ones of formula II-a by a novel reaction with a vinyl magnesium halide. Preferred halides are chloride, bromide and iodide. The reaction is conducted in the presence of an inert organic solvent, preferably an etheric reaction medium such as diethylether, diisopropylether, tetrahydrofuran, dioxane and the like. Surprisingly, it has been found that when the reaction is conducted under cold temperature conditions, the carbonyl group of the thus obtained vinyl-hydroxy compound of formula II-a is stable to further reaction with Grignard reagent. Thus, the reaction is suitably effected at a temperature of from −90°C. to 0°C. and preferably at a temperature of from about −70°C. to about −60°C. The order of addition of the reactants is not critical although it is generally preferred to add the vinyl magnesium halide to the pyran.

Alternatively, the hydroxy-non-1-en-3-ones of formula II-a can be obtained from the lactols of formula I via Steps (17) and (18) of Reaction Scheme B. Thus, the dihydroxy compounds of formula N are obtained by reacting the lactols of formula L with vinyl magnesium halide. The conditions employed for this reaction are not critical to this invention and are those normally employed in Grignard reactions. The reaction is normally conducted in the presence of an etheric reaction medium, such as diethylether, tetrahydrofuran and the like. The reaction is normally effected at a temperature of from about 0° to about 50°C.

In accordance with Step (18) of Reaction Scheme B, the 3-hydroxyl group of the dihydroxy compounds of formula N is selectively oxidized in known manner using manganese dioxide to yield the nonenones of formula L.

Because of the susceptibility of the vinyl group of the 7-hydroxy-1-nonen-3-ones of formula II-a to oxidation, it is desirable although not essential that these compounds be converted to more stable variants.

Thus, it is preferred to utilize the compounds of formulae II-a in the variant form of the hemiketals of the formula:

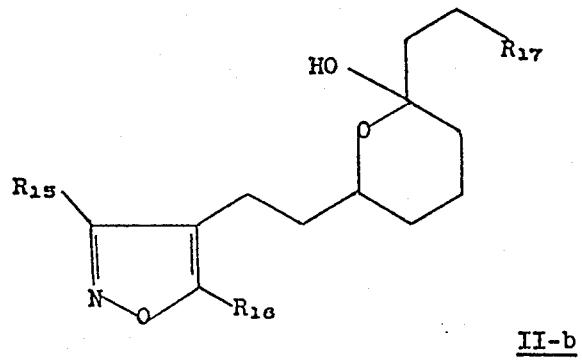

II-b wherein $R_{17}$, $R_{15}$ and $R_{16}$ are defined as aforesaid.

The internally hydrated Mannich base variants of formula II-b can be conveniently prepared without purification of the vinyl ketones II-a. The reaction sequence in accordance with Step (9) comprises adding to the crude vinyl ketone solution obtained in accordance with Step (8) above, a mono-hydrocarbylamine or di-hydrocarbylamine, to yield the Mannich base of formula II-b which is conveniently recovered from the solution by solvent removal. The compound may be readily purified by extraction into dilute acid.

Alternatively, the 7-hydroxy-1-alken-3-one compounds of the formula II-a can be converted to another stable variant of the formula:

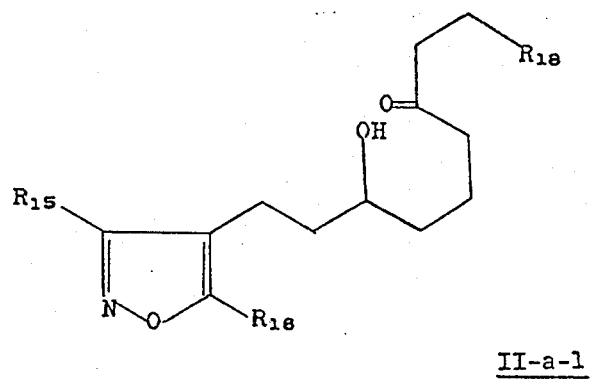

II-a-1 wherein $R_{15}$ and $R_{16}$ are defined as aforesaid and $R_{18}$ is chloro, hydroxyl, lower alkoxy, mono- hydrocarbylamino, di-hydrocarbylamino and acid salts of these amines.

Exemplary of the amines which may be employed to form the compounds represented by formulas II-b and II-a-1 are diethyl amine, methylbutylamine, butylamine, ethylbutylamine, cyclohexylamine, α-naphthylamine, diphenylamine, N-phenyl-2-naphthylamine or the like. Preferred are aliphatic primary or secondary lower hydrocarbyl amines, especially saturated lower hydrocarbyl secondary amines. Also preferred are the optically active amines described hereinafter.

The compounds of formula II-a-1 are readily produced from the vinyl ketones of formula II-a by known techniques, for example, 1-chloro-7-hydroxy-alkan-3-ones are obtained by the Markownikoff reaction of the vinyl compound with hydrogen chloride in a known manner. 1-Hydroxy and 1-alkoxy derivatives are obtained by the base catalyzed reaction of water or a lower alkanol, for example, methanol with the vinyl ketone. Additional derivatives are formed by the reaction of the vinyl ketone with a mono-hydrocarbyl amine or di- hydrocarbylamine as described above. In some instances, it may be desirable to convert the Mannich base to its crystalline acid addition salts. The acid salts of the amines of formula II-a-1 and similarly the hemiketals of formula II-b are conveniently obtained by reacting the amines with the desired anhydrous mineral or organic acid in a suitable aprotic solvent such as an ether or hydrocarbon. Preferred acids are hydrogen halides, especially hydrogen chloride and lower alkyl dicarboxylic acids, especially oxalic acid.

As is apparent, those compounds of formula II-a-1 wherein $R_{18}$ is mono- hydrocarbylamino, di-hydrocarbyl amino or acid salts of the amines and the compounds of formula II-b are isomers. These isomers exist in the ketone form of formula II-a-1 or in the cyclic hemiketal of formula II-b or as the equilibrium mixture of the two forms. Whether a particular Mannich base of formula II-a-1 exists in that form or the hemiketal form or in an equilibrium mixture consisting primarily of one or the other will depend upon the environmental conditions in which it is placed, such as temperature, solvent and pH of reaction medium, as well as the particular meaning of $R_{18}$ and $R_{17}$. Either form is useful for the purposes of this invention since these isomers are used in a reaction with compounds of formula III, infra, and either the acyclic forms of formulae II-a and II-a-1 or the cyclic hemiketal form of formula II-b is useful for this purpose. A particular advantage of the cyclic form is its greater stability as compared with the acyclic form and also as compared with the vinyl ketones of formula II-a-1. Acidic conditions shift the equilibrium away from the cyclic form.

The starting materials of the formulae II-a, II-a-1 and II-b can either be used in racemic form or in the optically active form. When used in an optically active form the 7Rantipode is required to give naturally occurring steroids.

The optically active forms of the formulae II-a, II-a-1 and II-b can be conveniently obtained by several routes. For example, by the use of an optically active amine such as α-phenethylamine, abietylamine or menthylamine, one can resolve these compounds via salt formation. Thus, by reaction with a lower alkyl dicarboxylic acid, e.g., oxalic acid or a hydrogen halide acid, e.g., hydrogen chloride, suitable salts can be formed. An optically pure antipode of formulae II-a-1 or II-b is thus obtained after separation of the salts, with optional conversion of the salts to the free amines by known means, e.g. by reaction with an alkali metal hydroxide. These compounds are then used in the remainder of the reaction sequence of this invention.

Alternatively, the optically active antipodes of formulae II-a-1, II-a and II-b can be prepared, in a manner analogous to that employed to obtain the racemic materials, from the optically active lactones of formula L. These lactones are prepared by the sequence of Steps (15), (16) and (7) of Reaction Scheme B. Thus, racemic lactones L are converted to the diastereomeric hydroxy esters or amides (Step 15) by reaction with an optically active alcohol, e.g., menthol, or an optically active amine, e.g., α-phenethylamine in a neutral solvent, preferably benzene, toluene or xylene and preferably at the reflux point of the solvents. The diastereomers of formula M are separated by crystallization or preparative gas phase chromatography. Optically active compounds of formula M are converted (Step 16) by treatment with an alkali metal hydroxide in alcohol or alcohol-water mixtures to the optically active hydroxy acids of formula K. A preferred reagent is sodium hydroxide in aqueous lower alcohol, preferably methanol at reflux. The optically active hydroxy acids of formula K are converted to the optically active lactones of formula L (Step 7) exactly as described previously for the racemic compounds, e.g., by thermal lactonization.

In still another method, the racemic lactones of formula L can be hydrolyzed to the corresponding hydroxy acids of formula K which can then be resolved by treatment with an optically active base, e.g., brucine, ephedrine or quinine and separating the thus obtained diastereomeric salts.

Still other methods will be apparent to those skilled in the art. Resolution can also be effected at a latter stage in the synthesis as will be more fully described hereinafter. The optically pure isomers of formulae II-a, II-a-1 and II-b are then used in the remainder of the reaction sequence of this invention and when coupled with the unique asymmetric induction and preservation of optical specificity thereof offer a facile route to optically pure steroidal materials.

In a further aspect, this invention is concerned with the compounds of formulae I-a, I-b, I-c, X and XI and their method of preparation via the general reaction scheme set forth in Reaction Scheme C.

Thus, in this aspect, this invention is concerned with novel cyclopenta[f][1]benzopyrans having the tricyclic nucleus

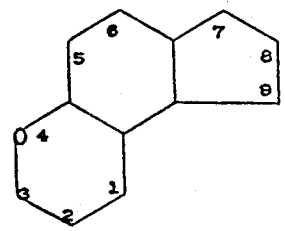

and novel naphtho 2,1-b pyrans having the tricyclic nucleus

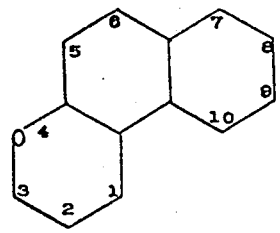

These novel compounds are generally defined by the formula:

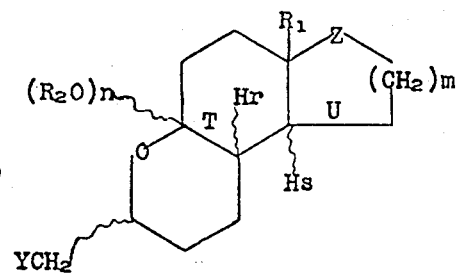

I wherein Y, Z, $R_1$, $R_{15}$ and $R_{16}$ are defined as aforesaid; T represents either a single or a double bond; U represents a single or a double bond and is a single bond when T is a single bond; m is an integer having a value of from 1 to 2; n is an integer having a value of from 0 to 1 and is 0 when T represents a double bond and is 1 when T represents a single bond; r is an integer having a value of from 0 to 1 and is 0 when T is a double bond and 1 when T is a single bond; and s is an integer having a value of from 0 to 1 and is 0 when U is a double bond and 1 when U is a single bond.

Preferred compounds are those wherein Y is defined so that $R_{15}$ and $R_{16}$ are both lower alkyl especially wherein both $R_{15}$ and $R_{16}$ are methyl — i.e., 3,5-dimethyl-4-isoxazolylmethylene; $R_1$ is n-alkyl, especially methyl and ethyl; and, when s has a value of 1, the 9α-(when m is 1) or 10α- (when m is 2) hydrogen is trans-oriented with respect to $R_1$.

Subgeneric to the tricyclic compounds of formula I are the 3-substituted-6αβ-alkyl-1,2,3,5,6,6a,7,8-octahydrocyclopenta-[f][1]benzopyrans and the 3-substituted-6αβ-1,2,5,6,6a,7-8,9-octahydro-3H-naphtho[2,1-b]pyrans, hereinafter referred to as "dienes" having the formula:

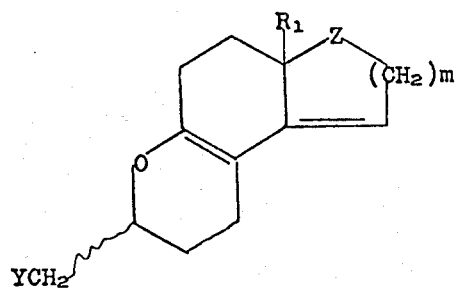

Ia wherein $R_1$, Z, Y and m are as defined above, the 3-substituted-6αβ-alkyl-1,2,3,5,6,6a,7,8,9,9a-decahydrocyclopenta[f][1]benzopyrans and the 3-substituted-6αβ-alkyl-1,2,5,6,6a,7,8,9,10,10a-decahydro-3H-naphtho[2,1-b]pyrans hereinafter referred to as "monoenes" represented by the formula:

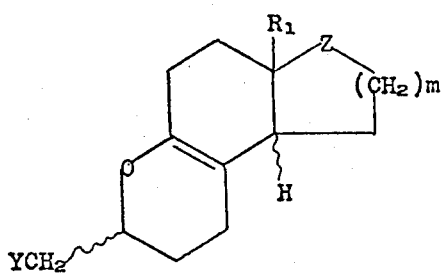

Ib wherein $R_1$, Z, Y and m are as defined above; and the 3-substituted-6αβ-alkyl-4a-hydroxyperhydrocyclopenta-[f][1]benzopyrans and the 3-substituted-6αβ-alkyl-4a-hydroxyperhydro-3H-naphtho[2,1-b]pyrans and their lower alkyl ethers and monoacyl esters; hereinafter referred to as "perhydro" compounds, represented by the formula:

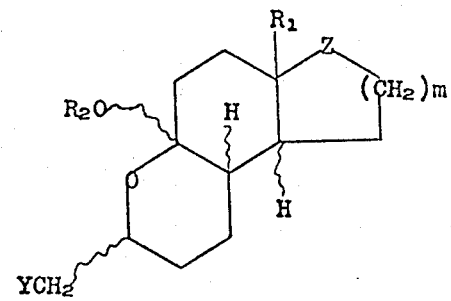

Ic wherein $R_1$, $R_2$, Z, Y and m are as defined above.

The second reactant employed in the condensation in accordance with Step (a) of Reaction Scheme C as generally mentioned above is a 2-(lower alkyl)cycloalkane-1,3-dione of the formula:

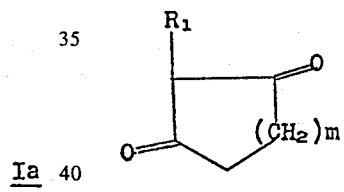

III wherein $R_1$, Z and m are as defined above. These compounds are known compounds and description of their synthesis is accordingly unnecessary. Suitable compounds include 2-methylcyclopentane-1,3-dione; 2-ethylcyclopentane-1,3-dione; 2-propylcyclopentane-1,3-dione; 2-butylcyclopentane-1,3-dione; 2-methylcyclohexane-1,3-dione; 2-ethylcyclohexane-1,3-dione and the like.

Thus, the process of this invention comprises in this aspect in accordance with Reaction Scheme C the general steps of (a) condensation of a 7-hydroxy-1-alken-3-one (II-a) or a variant thereof (II-a-1; II-b) with a 2-alkylcycloalkane-1,3-dione (III) to produce diene (I-a); (b) saturation of the 9,9a-or 10,10a-double bond of diene (Ia) to produce monoene (Ib); (c) introduction of a hydroxy, alkoxy, or acyloxy group at the 4a-position and a hydrogen atom at the 9b- or 10b-position of monoene (Ib) to produce perhydro (Ic); (d) oxidation of the perhydro compound of formula (Ic) to form the bicyclic compound of formula X and (e) cyclization of the bicyclic compound to produce benz[e]indene compounds of formula XI.

The conditions for the condensation of ketone (II-a) or variant (II-a-1 or II-b) with cyclic dione (III) are not narrowly critical, although it is preferred, particularly when the acyclic ketone is charged as the vinyl ketone, that a nonoxidizing atmosphere, e.g., nitrogen or argon, be employed. If desired, an antioxidant, for example, phenolic compounds such as hydroquinone may be employed. Furthermore, the reaction can be conducted in the absence or presence of acid or base promoters. Suitable basic promoters include those heretofore known to promote the Michael condensation, including inorganic bases, for example, alkali metal hydroxides, such as sodium hydroxide or potassium hydroxide and organic bases, including alkali metal alkoxides, for example, sodium or potassium methoxide or ethoxide, and ammonium hydroxides, particularly benzyltrialkylammonium hydroxides. A preferred class of base promoters are the amines, especially tertiary amines and most preferably pyridine-type compounds such as pyridine and the picolines. Acid promoters which can be employed include organic carboxylic acids such as acetic acid or benzoic acid; organic sulfonic acids such as p-toluenesulfonic acid; and mineral acids such as sulfuric acid, phosphoric acid, hydrochloric acid and the like. The amount of promoter employed is not narrowly critical and can vary from catalytic amounts to molar amounts.

The ratio of ketone (II-a) or variant (II-a-1 or II-b) to 2-lower alkyl-cycoalkane-1,3-dione (III) is not narrowly critical although approximately equimolar amounts are preferred. Although there is no particular advantage to the use of excesses of either reactant, the 2-alkyl-cycloalkane-1,3-dione can be more readily employed in excess because, due to its general low solubility in known organic solvents, unreacted cycloalkanedione can be easily recovered from the reaction mixture.

The reaction temperature is not critical and can vary from room temperature or below to reflux temperature or higher. The condensation is preferably conducted in the presence of an inert solvent to insure a fluid reaction mixture and uniform reaction temperatures. Primary alcohols are not desirable due to their tendency to react with vinyl ketones. Suitable solvents include tertiary alcohols such as tert.-butanol; aliphatic and aromatic hydrocarbons such as cyclohexane, hexane, octane, benzene, xylene, toluene and the like; ethers such as diethylether, tetrahydrofuran and the like; chlorinated hydrocarbons such as carbon tetrachloride, chloroform and the like; as well as dipolar aprotic solvents such as dimethylsulfoxide and the N,N-disubstituted amides such as dimethylformamide or dimethylacetamide.

The product of the condensation, depending upon the nature of the reaction promoter employed, can be one or both of the compounds having the formulae:

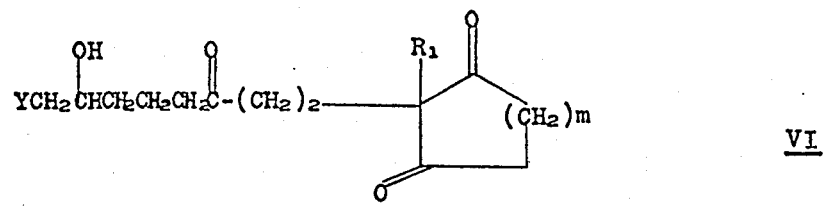

VI

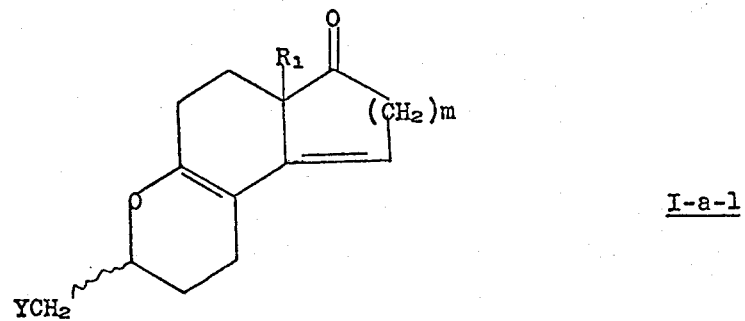

I-a-1 wherein $R_1$, Y and $m$ are as defined above.

When the promoter is an acid or a relatively weak base, such as pyridine, or when no promoter is employed at all, the reaction product obtained is the diene, i.e., the tricyclic enol ether (I-a-1). When a strong base, such as sodium or potassium hydroxide, is employed as a promoter, a crystalline product having the formula VI is isolated. However, the compounds of formula VI upon treatment with an acid, such as acetic acid, para-toluenesulfonic acid, or sulfuric acid, readily form the dione, i.e., tricyclic enol ether (I-a-1).

The dienes of formula I-a in the presence of water and acid, e.g., sulfuric acid in acetone, aqueous acetic acid or aqueous hydrochloric acid in dioxane, undergo acid hydrolysis to form indenones of the formula:

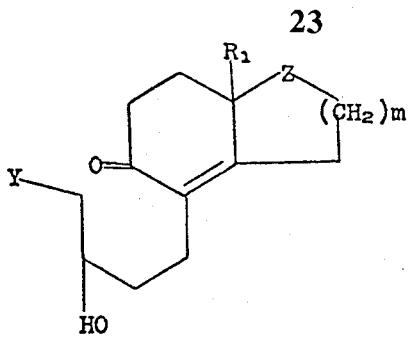

I-a'

The compounds of general formula I-a-1 as described above are readily converted to their corresponding derivatives of the formula:

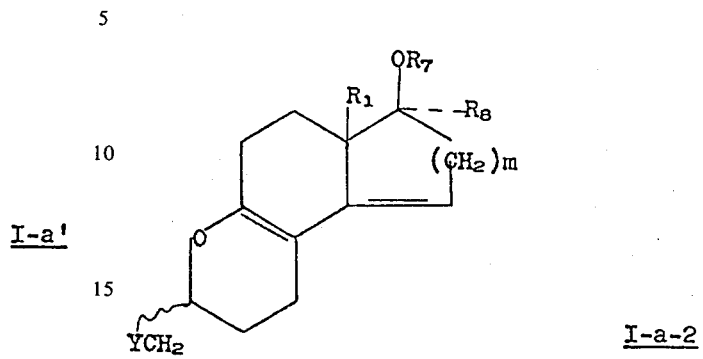

I-a-2 wherein $R_1$, Y and m have the same meaning as above.

The indenones of formula I-a' are themselves convertible to compounds of formula I-a via dehydration, for example, via acid catalyzed azeotropic distillation in benzene. Suitable acid catalysts are p-toluenesulfonic acid, potassium bisulfate, boron trifluoride etherate and the like. This reversible hydrolysis of compounds of formula I-a is useful in their preparation and purification. Thus, in instances where the direct purification of compounds of formula I-a is difficult it is often more facile to hydrolyze the compound of formula I-a to a compound of formula I-a', which can then be purified, for example, by chromatography, and subsequently be reconverted to the desired compound of formula I-a via dehydration.

The condensation of a vinyl ketone of formula II-a or a variant thereof of formulae II-a-1 or II-b with a cycloalkane-1,3-dione of formula III results in a specific stereochemical induction at one member of the critical C/D-ring junction. Thus, this invention is particularly advantageous in that it involves a unique asymmetric induction. The products of the condensation, i.e., the dienones of formula I-a, have at least two asymmetric centers at positions-3 and -6a permitting theoretically of two racemates or four optical antipodes. However, as a result of the condensation described in this invention, when using a racemic starting material of formulae II-a, II-a-1 or II-b only a single racemate of formula I-a results and when using an optically active starting material of formulae II-a, II-a-1 or II-b, only a single optical antipode of formula I-a results. It has further been found that when starting with a compound of formulae II-a, II-b or II-a-1 with a 7R-configuration there is obtained the more desirable optical antipode of formula I-a having a 6aβ-absolute configuration. Thus, to prepare steriodal materials having the more desired 13β-absolute configuration by the synthesis of this invention one can either start with the 7R-antipode of formulae II-a, II-a-1 or II-b which can be prepared by the methods described aforesaid or one can resolve at some intermediate stage subsequent to the condensation with a cycloalkanedione of formula III or one can resolve the end-product steriodal material. In any event, the unique asymmetric induction concurrent to the condensation of this invention renders the obtention of a single optical antipode as an end-product more facile.

wherein Y, $R_1$, $R_7$, $R_8$ and m are as previously defined.

Thus, the ketodienes of formula I-a-1 are readily converted to the corresponding 7β-alcohols and their esters or ethers as represented by the formula I-a-2 above by the sequence of reactions comprising reduction of the ketone to the alcohol and, if desired, subsequent esterification or etherification.

The reduction can be effected by any of several known methods for the chemical reduction of a ketone, e.g., by reaction of dienone (I-a-1) with a group III-metal reducing agent. Group III-metals include those having atomic numbers of from 5 to 13, inclusive, i.e., boron and aluminum. Illustrative examples of these reducing agents include tri(lower alkoxy)aluminum compounds such as triisopropoxyaluminum; di(lower alkyl)aluminum hydrides such as diethylaluminum hydride and diisobutylaluminum hydride; alkali metal-Group III-metal complex hydrides such as lithium aluminum hydride, sodium aluminum hydride, and sodium borohydride; tri(lower alkoxy)alkali metal-Group III-metal complex hydrides such as trimethoxy lithium aluminum hydride and tributoxy lithium aluminum hydride and the like. The alkali metal-Group III-metal complex hydrides are preferred as reducing agents, with lithium aluminum hydride being especially preferred.

This reaction is effected in any suitable inert reaction medium such as hydrocarbons, e.g., cyclohexane, benzene, toluene and xylene or ethers, e.g., diethylether, diisopropylether and tetrahydrofuran. Protic solvents such as water or alcohols should not be employed when lithium aluminum hydride is the reducing agent, but can be employed with sodium borohydride.

The remaining reaction conditions are not narrowly critical, although it is generally preferred to effect the reduction at reduced temperatures, i.e., below room temperature (about 20°–25°C.). Temperatures in the range of from about 0°C. to about room temperature are normally employed.

The free alcohol is recovered from the reaction mixture after treatment of the mixture with acid. The alcohol can be esterified in known manner, for example, by base-catalyzed reaction with a carboxylic acid halide or carboxylic acid anhydride. Illustrative bases include inorganic bases such as sodium hydroxide and potassium hydroxide and organic bases such as a sodium alkoxide or an amine, especially a tertiary amine, and more particularly, pyridine and the picolines. Similarly, the alcohols can be reacted in a known manner to yield the ethers of formula I-a-2.

The ketodienes of formula I-a-1 can also be converted to their 7β-hydroxy-7α-hydrocarbyl derivatives represented by the formula I-a-2 above by reaction with a Grignard reagent of the formula:

$$R_8MgT \qquad \qquad VII$$

wherein $R_8$ is as previously defined and T is a halogen having an atomic number of from 17 to 35 inclusive (i.e., chlorine or bromine).

This Grignard reaction is conducted in a known manner. For example, the Grignard reagent is prepared by reacting a hydrocarbyl halide with magnesium in an ether reaction medium, for example, ethylether or tetrahydrofuran at elevated temperature, generally in the range of from about 30°C. to about 75°C. The ketodiene compound I-a-1) is then added to the Grignard solution at about room temperature, although higher or lower temperatures can be employed. The resulting reaction product is hydrolyzed to produce the free alcohol, which can be esterified or etherified as discussed above.

The second step of the general synthesis of the tricyclic compounds of this invention comprises conversion of the dienes of formula I-a to the monoenes of formula I-b in accordance with Reaction Scheme C by a selective catalytic hydrogenation. The hydrogenation must be conducted under mild process conditions so as to avoid hydrogenating the isoxazole moiety. Suitable noble metal catalysts are palladium, platinum and rhodium with the preferred catalyst being palladium. These catalysts can be employed in the form of the metal alone, or can be deposited on suitable support materials, such as carbon, alumina, calcium carbonate, barium sulfate and the like. The hydrogenation is preferably conducted in the presence of inert solvents such as hydrocarbons, alcohols, ethers and the like. The reaction conditions of pressure and temperature are critical. Thus, the hydrogenation is effected at a pressure of about one atmosphere and a temperature of about room temperature. These ambient conditions are generally preferred to avoid significant hydrogenation of the 4a,9b(10b)-double bond or the isoxazole moiety. The hydrogenation medium can be acidic or neutral as may be desired, although a neutral media, such as hydrocarbons, e.g., toluene or hexane is preferred for best results. Optionally, the reaction medium can include mono, di or tri-alkyl amines. In general, hydrogenation of the diene of formula I-a leads to the corresponding monoene of formula I-b.

Via the aforesaid catalytic hydrogenation, monoenes of formula I-b having a C/D-trans ring junction are formed in a major proportion when hydrogenating a diene of formula I-a-2. This method thus provides an advantageous synthesis of C/D-trans steroidal materials. When hydrogenating a diene of formula I-a-1, C/D-cis compounds are formed in a major proportion. This method thus provides an advantageous synthesis of C/D-sis steroidal materials. However, when the dienes are intermediates for the synthesis of steroids having the C/D-trans-orientation, this technique of using the free carbonyl derivative is not particularly desirable. When monoenes of formula I-b having C/D-trans configuration are desired, it is preferable to first reduce the dienone of formula I-a-1 to a corresponding hydroxy compound of formula I-a-2 as described aforesaid prior to the catalytic hydrogenation. Following the catalytic hydrogenation, the cabonyl moiety in formula I-b-1 can be regenerated by conventional means, such as oxidation with chromium trioxide, if desired.

The monoenes of formula I-b prepared by the above-described hydrogenation contain at least three asymmetric centers, at positions -3, -6a and -9a when m is one and at positions -3, -6a and -10a when m is two. With respect to these three centers, there are thus eight antipodal configurations possible. By virtue of the unique asymmetric induction described in this invention, proceeding from a racemic starting material of formulae II-a, II-a-1 or II-b, only four of these antipodes of formula I-b are prepared and proceeding from an optically active starting material of formulae II-a-1, II-a or II-b, only two of these antipodes of formula I-b are prepared. Moreover, by the above-described hydrogenation, there can predominantly be prepared one antipode, having the desired 6a,9a(10)-trans-ring juncture. Thus, the eventual obtention of the more desired 13β-C/D-trans-configuration in the ultimate steroidal products is rendered more facile by the stereoselective reactions provided by this invention.

The monoenes of formula I-b are converted to the perhydro compounds of formula I-c by reacting the monoene with a compound having the formula:

$$R_2OH \qquad \qquad VIII$$

wherein $R_2$ is as previously defined.

That is, the monoene of formula I-b is reacted with water, a primary alcohol, or a carboxylic acid. This reaction is catalyzed by mineral or organic acids, for example, hydrochloric acid, phosphoric acid, sulfuric acid, para-toluenesulfonic acid, and the like. Sulfuric acid is the preferred acid catalyst and water the preferred reactant. Although not necessary, it is desirable to conduct this reaction in the presence of an added solvent, particularly in the event the compound of formula VIII is water. In this case, it is desirable to employ a solvent which is both miscible with water and a solvent for the monoene of formula I-b. Solvents of this nature include acetone, tert.-butanol, dioxane and the like. The reaction temperature is not critical and ambient temperature is normally employed, although higher and lower temperatures could be employed if desired.

It should be noted that the perhydro compounds of formula I-c can also exist in equilibrium with an open isomeric form of the formula Ic-1

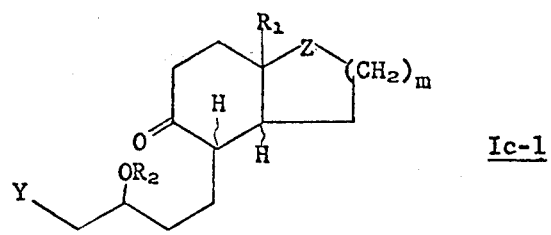

Ic-1 wherein $R_1$, $R_2$, Z, $m$ and Y are as defined aforesaid.

Under the process conditions employed in the instant synthesis the cyclic form of the formula I-c predominates in the equilibrium mixture.

The compound of formula I-c is oxidized to form the bicyclic compound of the formula X in accordance with Step (d) of Reaction Scheme C by contact with an oxidizing agent such as chromic acid, potassium dichromate, or potassium permanganate. Jones reagent (chromium trioxide and aqueous sulfuric acid with acetone as solvent), or a chromic acid-acetic acid mixture is preferred as oxidizing agent. The nature of Z is unchanged in this reaction, except when Z is hydroxymethylene [—CH(OH)—]. In this instance, unless the hydroxyl group is protected, as by formation of a lower acyl ester, it is oxidized to form a carbonyl group. Further, if Z is a ketal, if may be cleaved to form the free carbonyl group. The reaction temperature is not narrowly critical and temperatures in the range of from 0°C. to about 75°C. are suitable, although ambient temperature is preferred.

The bicyclic compound (X) is treated with acid or base to effect cyclization to the tricyclic compound of formula (XI) in accordance with Step (e) of Reaction Scheme C. In this reaction, it is preferred that the water of reaction be removed when acidic conditions are employed as by refluxing the reaction mixture with an azeotroping agent and separating the water from the condensate. Suitable strong acids are sulfuric acid, p-toluenesulfonic acid, potassium bisulfate and the like. Alternatively, base catalyzed dehydration can be utilized, for example, by refluxing compound (X) in the presence of methanolic sodium hydroxide. It should be noted that when starting with a C/D-trans enol ether of the formula I-b, a trans-anti configuration will be obtained in the enone of the formula XI, i.e, the $C_8$ hydrogen (Steroid numbering) will be beta.

Alternatively, compounds of the formula XI-b

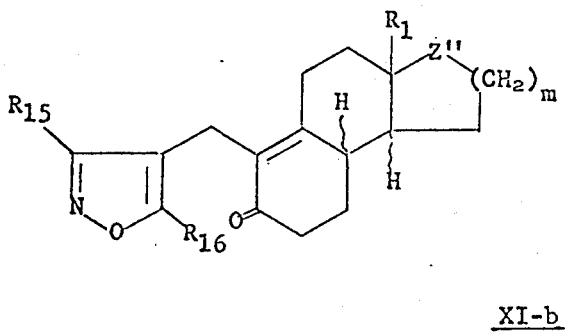

XI-b can be prepared from 1,2,3,3a,4,5,8,9,9a,9b-decahydro-3aβ-alkyl-7-oxo-7H-benz[e]indenes and 4,4a,4b,5,6,7,8,8a,9,10-decahydro-8aβ-alkyl-3H-phenanthren-2-ones wherein the 6 and 1 positions respectively are substituted with hydrogen, by alkylation with a 4-halomethyl isoxazole. The reaction is suitably conducted in an organic solvent such as 1,2-dimethoxyethane, dimethylsulfoxide, or a lower alcohol, e.g., ethanol in the presence of a strong base such as an alkali metal alkoxide, e.g., sodium methoxide or an alkali metal hydride, e.g., sodium hydride. The reaction can be conducted at a temperature range of from room temperature to the reflux temperature of the solvent.

A further aspect of this invention relates to the process and intermediate compounds employed to convert the benz[e]indenes and phenanthren-2-ones of formula XI-a in accordance with Reaction Scheme D to 19-nor-steroids of the formula XIV-a.

The cycloolefin compounds of formula XI-a are hydrogenated to the tricyclic compounds of formula XV in accordance with Step (f) of Reaction Scheme D. The hydrogenation is preferably effected in a lower alcohol solvent, e.g., ethanol using a palladium metal catalyst and carbon carrier although other noble metal catalysts may be employed. The hydrogenation is conducted under neutral, acidic or weakly basic conditions substantially at atmospheric pressure and room temperature so as to selectively hydrogenate the $\Delta^{9(10)}$ -bond without substantially hydrogenating the isoxazolyl moiety. Suitable weak bases for this purpose are mono, di or tri-lower alkyl amines, preferably triethyl amine. It has been found that the use of base in this hydrogenation step aides in selectively promoting the formation of the compound of formula XV which has a trans-anti-trans configuration when trans-anti enones of formula XI-a are employed as reactants.

Use of aqueous hydrobromic acid, e.g., 0.003–10 mole equivalents of HBr with a 0.1–20 percent Pd/BaSO$_4$ catalyst in a lower alkanol, e.g., methanol or ethanol, in this hydrogenation step results in the promotion of the selective formation of the compounds of formula XV which have a trans-anti-cis configuration when the trans-anti-enones of formula XI-a are employed. In this reaction pressures of preferably about 1 atm. and a temperature of about room temperature may be conveniently employed.

The conversion of the tricyclic compounds of formula XV to the steroids of formula XIV-a can be accomplished by three alternative reaction methods. Thus, process routes (1), (m), (o) and (K') hereinafter referred to as the "heterocyclic anhydrous basic route" and (1), (m'), (o') and (k') hereinafter referred to as "heterocyclic aqueous basic route" exemplified in Reaction Scheme D can be employed. The third method is described in Reaction Scheme D'.

At this point in the process, it should be noted that all hydrogenations conducted thus far viz, Steps (3) and (12) of Reaction Scheme B, Step (b) of Reaction Scheme C and Step (f) of Reaction Scheme D have been carefully conducted under mild hydrogenating conditions, i.e., in the absence of strong base and substantially at room temperature and atmospheric pressure to selectively avoid hydrogenating the isoxazole moiety to any significant degree. However, the isoxazole group can now be readily cleaved as described hereinafter.

The tricyclic compounds of formula XV can be converted to the 19-nor-steroids of formula XIV-a via the "heterocyclic anhydrous basic route" which comprises sequential process Steps (1), (m), (o) and (k') of Reaction Scheme D. Thus, the vinylogous amides of formula XXVII can be obtained from the tricyclic compounds of formula XV via Step (1), in the same reaction mixture that was employed to hydrogenate the compounds of formula XI-a to the compounds of formula XV[Step (f)], by the addition of strong base to the reaction medium and then further hydrogenating. Alternatively, hydrogenation of the isoxazole group of the isolated compound XV can be suitable conducted in the presence of a catalyst, preferably, a noble metal catalyst, such as rhodium, palladium, platinum, and the like or Raney nickel. The catalyst can be utilized with or without a carrier and if a carrier is used, conventional carriers are suitable. Especially preferred is 10 per cent Pd/C. The ratio of catalyst to substrate is not critical and can be varied. However, it has been found advantageous to use a weight ratio of catalyst to substrate from about 1:5 to about 1:25. Especially preferred is a ratio of 1:10. The hydrogenation is suitably effected in an organic solvent, preferably a lower alcohol at room temperature and atmospheric pressure in the presence of strong base, although higher temperatures and pressure may be employed. Preferred bases for the second hydrogenation are strong alkali metal hydroxides, e.g., potassium hydroxide, sodium hydroxide and the like. Treatment of the vinylogous amides of formula XXVII with anhydrous base, in accordance with Step (m) of Reaction Scheme D, results in dehydration and acyl cleavage of the compounds of formula XXVII to yield the dihydro pyridines of formula XXVIII. Preferred anhydrous bases for this conversion are alkali metal lower alkoxides, especially sodium ethoxide. The reaction is conveniently carried out in a lower alcohol solvent, preferably ethanol. Hydrolysis of the substituted dihydropyridines of formula XXVIII with aqueous alcoholic base in accordance with Step (o) of Reaction Scheme D yields the diketone compounds of formula XIII'. Cyclization of the latter compounds, which are not isolable, occurs rapidly to give 19-nor-steroids of formula XIV-a in accordance with Step (k') of Reaction Scheme D.

It should be noted when employing the anhydrous basic route tha the acyl group

is selectively cleaved, thus enabling use of mixed isoxazoles, e.g., those wherein $R_{15}$ and $R_{16}$ are not identical. This route thus permits obtention of uniform steroidal products vis. — those substituted at the steroidal C-4 position solely with an $R'_{15}$ substituent.

19-Nor-steroids of formula XIV-a can alternatively be obtained from the vinylogous amides of formula XXVII via sequential process steps (m'), (o') and (k') - viz., the heterocyclic aqueous basic route. The most significant difference between the heterocyclic aqueous basic route and the heterocyclic anhydrous basic route described immediately aforesaid, lies in the difference between process Steps (m) and (m'). In the former case, strong anhydrous base is employed in Step (m) yielding heterocyclic compounds of formula XXVIII and in the latter case strong aqueous base such as, for example, aqueous metal hydroxides, preferably NaOH, is employed in Step (m') yielding triketones of formula XXLX. It should be noted, however, that the aqueous basic route is not selective and probably also proceeds via Step (m) as well as Step (m'). The diketones of formula XIII', which are obtained in accordance with Step (o') by cleaving the triketones of formula XXIX, further react by cyclizing (Step K') to yield steroids of formula XIV-a. The acyl cleavage effected in accordance with Step (o') is not selective, that is to say it is not possible to predict whether the

group or the

acyl group will be cleaved. It is, therefore, desirable when employing the aqueous basic route that $R_{15}$ and $R_{16}$ be identical or either $R_{15}$ or $R_{16}$ be hydrogen in order to avoid the obtention of mixed steroidal products. If either $R_{15}$ or $R_{16}$ is hydrogen, selective cleavage of the formyl group occurs, thus avoiding mixed steroidal products.

It should be emphasized as one further facet of the stereoselectivity of the instant invention, that when tricyclic compounds of formula XV having a trans-anti-trans-configuration are employed in Reaction Scheme D, steroids of formula XIV-a having a trans-anti-trans-anti-configuration are produced. This is highly desirable since many pharmacologically valuable compounds possess this configuration.

Furthermore, when tricyclic compounds of formula XV having a trans-anti-cis configuration are used in Reaction Scheme D, steroids of formula XIV-a having a trans-anti-cis-anti-configuration are produced. These compounds are 19-nor-9β,10α-steroids which are also known as 19-nor-retrosteroids and form a further class of pharmacologically valuable compounds.

In compounds represented by the formulae XXVII, XXVIII and XIII' of Reaction Scheme D, Z' is defined in an identical manner to Z as defined aforesaid, with the proviso that Z' can not be a lower alkylenedioxymethylene, phendioxy-methylene or dialkoxymethylene or ester function. However, the end-products of formula XIV-a substituted in the 17-position (steroidal numbering) by Z are obtained from the precursors of the formulas which are substituted in the 17-position by Z' by means known in the art.

When effecting the conversion of benz[e]indenes and phenanthren-2-ones of formula XI-a to the steroids of formula XIV-a via either the heterocyclic aqueous basic group or the heterocyclic anhydrous basic group in accordance with Reaction Scheme D, variable amounts of pyridines are produced even when oxygen is excluded from the reaction medium. These pyridine products presumable arise from oxidation or disproportionation of some of the intermediates.

Therefore, another aspect of this invention relates to the process and intermediate compounds employed to convert the tricyclic compounds of formula XV to the steroids of formula XIV-a in accordance with Reaction Scheme D' via process Steps (g), (h), (i), (j) and (k) which avoids the formation of pyridine intermediates and thereby correspondingly raises the yield of steroids produced. Pyridine formation is avoided in accordance with teachings of this invention by preventing cyclization to the vinylogous amides of formula XXVII (Reaction Scheme D) by first protecting the 7-position of the tricyclic compounds of formula XV prior to hydrogenating the isoxazole moiety.

The protected compounds of formula XXV are obtained from the tricyclic compounds of formula XV in accordance with Step (g) of Reaction Scheme D' by converting the free oxo group of the compounds of formula XV to a group represented by Z'' as defined aforesaid. This protection can be effected by ketalization to form the phendioxy-methylene, lower alkylenedioxy-methylene, dilower alkoxy-methylene, or the monothia, monoaza, or dithia chalcogen thereof by means known in the art. Preferred ketals are 1,2-ethylenedioxy, 2,3-butylenedioxy, and 2,2-dimethyl-1,3-propylenedioxy which can be obtained by reaction of the compounds of formula XV with the corresponding alcohols in a known manner. Alternatively, the oxo moiety can be converted to its dithia ketal by reaction with dithioethane in a known manner, for example, in acetic acid at room temperature and in the presence of boron trifluoride. Moreover, a monothia ketal can similarly be prepared in a known manner, for example, by reaction of the oxo moiety with 2-mercaptoethanol in dioxane at room temperature in the presence of zinc chloride and sodium sulfate. Also, the monoaza ketals can be prepared in a known manner, for example, by reaction of the oxo moiety with 2-hydroxyethylamine in the presence of acid.

Further, the oxo moiety can be reduced to the corresponding hydroxy compound with for example, sodium borohydride at low temperature and can then be etherified or esterified. A preferred ether protecting group is tertiarybutoxy which can conveniently be obtained from the corresponding hydroxy derivative by reaction under acid conditions with isobutylene by means known in the art.

The oxo moiety can be regenerated from its protected form at any desired stage of the reaction sequence. Thus, it can be readily produced by hydrolysis of the alkylenedioxy ketals in a known manner. Similarly, it can be regenerated from the dithia ketal in a known manner, for example, by treatment with phenylmercuric chloride and calcium carbonate in ethanol or by treatment with methanolic hydrochloric acid. Also, it can be regenerated from a monothia ketal in a known manner, for example, by treatment under strongly acidic conditions, for example, by treatment with aqueous sulfuric acid in dioxane or hydrochloric acid in acetic acid. Moreover, it can be regenerated from a monoaza ketal in a known manner, for example, by treatment with a strong aqueous acid. Also, ethers and/or esters can be reconverted to the free hydroxy group which in turn can be oxidized to give the oxo moiety.

The protected compounds of formula XXV are hydrogenated in accordance with Step (h) of Reaction Scheme D' to yield the vinylogous amides of formula XXVI. The hydrogenation is conducted under process conditions suitable to hydrogenate the isoxazolyl groups. A catalyst, preferably a noble metal catalyst, such as platinum, palladium and the like or Raney nickel or the like is employed. Especially preferred is the palladium catalyst. The nobel metal catalyst can be utilized with or without a carrier and if a carrier is used, conventional carriers are suitable. It is preferred to use palladium on carbon. Especially preferred is 10 percent Pd/C. The ratio of catalyst to substrate is not critical and can be varied. However, it has been found advantageous to use a weight ratio of catalyst to substrate from about 1:5 to 1:25. Especially preferred is a ratio of 1:10. The hydrogenation is suitably effected in the presence of strong base, preferably an alkali metal hydroxide, e.g., potassium hydroxide in an inert organic solvent for example, lower alcohols, e.g., methanol, ethanol or isopropanol. The reaction conditions of pressure and temperature are not narrowly critical as is the case when it is desired to avoid hydrogenating the isoxazole moiety. Therefore, if desired, pressures above one atmosphere and temperatures above room temperature may be suitably employed.

The vinylogous amides of formula XXVI are hydrolyzed to the diketones of formula XXX in accordance with Step (i) and cleaved in accordance with Step (j) of Reaction Scheme D' to yield the ketones of formula XIII using aqueous alkali hydroxide, preferably sodium hydroxide. The acyl cleavage effected in accordance with Step (j) is not selective. It is not possible to predict whether the

group or the

acyl group will be cleaved. It is, therefore, desirable when employing this route that $R_{15}$ and $R_{16}$ be selected so as to be identical or in the alternative either $R_{15}$ or $R_{16}$ be hydrogen to avoid the obtention of mixed steroid products. It should be noted, that if the function at position C-17 (steroid numbering) is an ester, it will be cleaved to the free alcohol under the conditions employed in Steps (i) and (j).

Treatment of the ketone of formula XIII wherein Z'' is a ketal function with a mineral acid, preferably hydrochloric acid in a lower alcohol solvent, suitably methanol at reflux, yields the steroids of formula XIV-a via Step (k) of Reaction Scheme D' by a process sequence of removal of the protecting group and cyclization. For cases wherein the protecting group Z'' of the ketone of formula XIII is other than a ketal function, the group is first removed and the free carbonyl group is regenerated by known methods, e.g., in the case of an alcohol with an oxidizing agent such as Jones reagent, prior to cyclization (Step k).

It should be noted that the process steps carried out in Reaction Scheme D' are stereoselective viz — if the tricyclic compounds of formula XV have a trans-anti-trans-configuration the steroid products of formula XIV-a have a trans-anti-trans-anti-configuration while if the tricyclic compounds of formula XV have a trans-anti-cis configuration the steroid products of formula XIV-a have a trans-anti-cis-anti-configuration.

In compounds represented by formulae XXV, XXVI and XIII of Reaction Scheme D, Z'' is defined in an identical manner to Z, as defined aforesaid, with a proviso that Z'' can not be a a free carbonyl function. However, the end products of formula XIV-a substituted in the 17-position by Z are obtained from the precursors of formula XIV-a which are substituted in the 17-position by Z'' by means known in the art.

Still another aspect of this invention relates to the process and intermediate compounds employed to convert the benz[e]indenes and phenanthren-2-ones of the formula XI-a in accordance with Reaction Scheme E to the estrones of the formula XXXVI.

The enones of formula XI-a are converted to the protected $\Delta^{9(11)}$-compounds of formula XXXI in accordance with Step (a) of Reaction Scheme E, wherein $R_1$, $R_{15}$, $R_{16}$, Z, Z'', W, V and m are defined as aforesaid. Protection can be effected by ketalization of the free carbonyl group of the compound of the formula XI-a via methods previously described (Step g, Reaction Scheme D'). Preferred ketals are 1,2-ethylenedioxy, 2,3-butylenedioxy, 2,2-dimethyl-1,3-propylenedioxy and the like. As is evident from the structure of compounds of formulae XI-a and XXXI ketalization results in isomerizing the $\Delta^{9(10)}$-unsaturated compounds to the $\Delta^{9(11)}$-unsaturated compounds.

The protected compounds of formula XXXI are hydrogenated in accordance with Step (b) to yield the $\Delta^{9(11)}$-vinylogous amides of formula XXXII. The hydrogenation is conducted under identical conditions employed for the hydrogenation in accordance with Step (h) of Reaction Scheme D. Unexpectedly, it has been found in accordance with the teachings of this invention that the hydrogenation of the compound of formula XXXI is selective, that is only the isoxazole moiety is hydrogenated without hydrogenating the $\Delta^{9(11)}$-unsaturated bond to any significant degree.

The resulting vinylogous amide of formula XXXII is treated as before, e.g., Steps (i) and (j) of Reaction Scheme D' with aqueous alkali metal hydroxide base to yield the $\Delta^{9(11)}$-ketones of formula XXXIII. The $\Delta^{9(10)}$-diketones of formula XXXIV are obtained from the $\Delta^{9(11)}$-ketones of formula XXXIII in accordance with Step (d) of Reaction Scheme E by treatment with aqueous mineral or organic acid, preferably acetic acid at a temperature range of 50°C. to the reflux temperature of the solvent.

The diketo $\Delta^{9(10)}$-compounds of formula XXXIV can be converted to the $\Delta^4$, $\Delta^{9(10)}$-steroids of formula XXXV. In a specific embodiment, the diene of formula XXXV, wherein Z is carbonyl, $R'_{15}$ is hydrogen, $R_1$ is methyl and m is 1 can be isomerized to the pharmaceutically valuable compound of formula XXXVI (estrone) via Step (f) of Reaction Scheme E if the trans-anti-stereoisomer of formula XI-a is used as a starting reactant. These methods of Steps (e) and (f) are more fully described in French Pat. No. 1,305,092, Assignee Roussel-Uclaf.

The compound of formula XIV-a, Reaction Scheme D', wherein Z is carbonyl, m is 1, $R_1$ is ethyl and $R'_{15}$ is hydrogen (19-nor-18-homo-androst-4-ene-3,17-dione), can be selectively alkynylated by a suitable organo metallic acetylide affording norgestrel (13β-ethyl-17α-ethinyl-17-hydroxy-gon-4-ene-3-one), a known progestational agent. Exemplary of the suitable alkynylating agents to effect the conversion to norgestrel are the alkali acetylides such as lithium acetylide, potassium acetylide, sodium acetylide and the like. The reaction is carried out in the presence of liquid ammonia in a suitable solvent system such as benzene or toluene. The alkynylation is effected preferably at the reflux temperature of the reaction medium although temperatures from −60°C. to 30°C. are suitable. Exemplary of other suitable reagents to effect the acetylenic addition is lithium acetylide diamine complex in dimethylformamide as solvent.

Compounds of formula XIV-a wherein Z is carbonyl can be converted into corresponding pharmaceutically valuable known pregnane compounds i.e., compounds of which Z is of the formula:

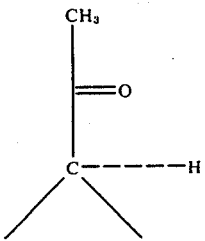

by known procedures. (Cf., U.S. Pat. No. 3,383,385, Bucourt et al.). These procedures for converting androstan-17-ones into pregnanes are best effected if all carbonyl groups other than that at C-17 are initially protected. Thus, for example, 19-nor-14β-androst-4-ene-3,17-dione can be converted into 19-nor-14β-17α-progesterone.

The 19-nor-compound of formula XIV-a, Reaction Scheme D', wherein m is 1, $R_4$ is propyl and $R'_{15}$ is hydrogen are ovulatory inhibitors [cf., Tetrahedron Letters, 127 (1967), Velluz et al.]. Additionally, compounds of formula XIV-a wherein $R_1$ is methyl, $R'_{15}$ is hydrogen, m is 1 and Z is carbonyl have been converted to 19-nor-testosterone acetate, J. Org. Chem., 26, 3904 (1961), L. J. Chinn et al.

Compounds of formula XIV-a of Reaction Scheme D' having the trans-anti-cis-anti configuration have been described in the literature. Thus racemic 19-nor-9β, 10α-androst-4-en-3,17 -dione (Z is carbonyl, m is 1, $R'_{15}$ is hydrogen and $R_1$ is methyl) is disclosed by Torgov et al., Chemistry of Natural Compounds, 1, 138 (1965). Optically active 19-nor-9β,10α-testosterone (Z is hydroxymethylene, m is 1, $R'_{15}$ is hydrogen and $R_1$ is methyl) was described by Velluz et al., Comptes Rendues, 252, 3903 (1961) while the 17α-methyl derivative of this compound is described by Farkas et al., J. Org. Chem, 34 3022 (1969).

As has been pointed out above, the products of this invention are produced in the form of various optically active antipodes, which can be carried through the entire reaction sequence, or which can be resolved at suitable places during the reaction sequence. For example, at any stage wherein a compound having a secondary hydroxyl group is present, one can react the secondary alcohol with a dicarboxylic acid to form a half ester. Suitable dicarboxylic acids include lower alkyl dicarboxylic acids such as oxalic acid, malonic acid, succinic acid, glutamic acid, adipic acid, or aromatic carboxylic acids such as phthalic acid. The resulting half-ester is then reacted with an optically active base, such as brucine, ephedrine, or quinine, to produce a diastereomeric salt. The salts, after separation, are then readily reconverted to optically active alcohols. As an alternative, the secondary alcohol can be reacted with an optically active acid, for example, camphorsulfonic acid. The resulting diastereomeric esters are then separated and reconverted to the alcohols.

It is preferred that the resolution be effected at some stage in the synthesis of the compounds of formulae II-a, II-a-1 or II-b as by the resolutions heretofore described. Resolution at such early stages in the overall process described herein is highly preferred because of the improved efficiency in the production of steroids having a desired configuration. Because the condensation of the alken-3-one or variant (II-a-1, II-a or II-b) with cycloalkanedione (III) is stereo-specific, as are the subsequent reaction steps, one, by proper selection of stereoisomers at these early stages, can ensure that substantially all of the tricyclic compounds of this invention and the steroids derived therefrom have a selected configuration. Thus, by this technique, the production of compounds of the undesired configuration is minimized or prevented entirely, with an attendant increase in the efficiency of the production of compounds of the desired configuration.

A further aspect of the present invention relates to novel 19-nor-retrosteroids of the formula

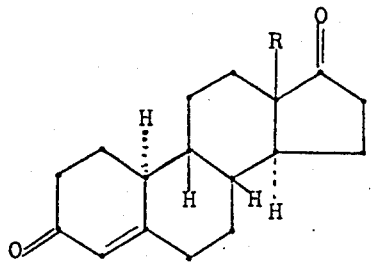

XXXVI where R is lower alkyl with at least 2 carbon atoms.

Compounds of formula XXXVI are anabolic, androgenic agents with a favorable anabolic/androgenic ratio. They are pituitary inhibitors, anti-estrogenic and lower cholesterol level in blood.

In the claims, all compounds should be construed to include, independently, the racemic form of the compound and independently each enantiomeric form unless specifically indicated otherwise.

The following examples are illustrative but not limitative of the invention. All temperatures are stated in degrees centigrade. Infrared, ultraviolet and nuclear magnetic resonance spectra where taken were consistent with exemplified structures.

EXAMPLE 1

Preparation of 4-carboethoxy-3,5-dimethylisoxazole

A solution of 320 ml. (325 g. = 2.5 moles) of ethyl acetoacetate, 209 ml. (178 g. = 2.5 moles) of pyrrolidine and 600 ml. of reagent grade benzene was heated at reflux with azeotropic removal of water for two hours. The benzene was then removed at reduced pressure and the residue was distilled through a 10-cm. Vigreux column yielding 427 g. of ethyl β-pyrrolidineocrotonate as a light yellow liquid, b.p. 155°–156°/10 mm.

A solution of the ethyl β-pyrrolidinocrotonate (427 g. = 2.33 moles), 190 ml. (182 g., 2.43 mole) of nitroethane and 1300 ml. of triethylamine in 1200 ml. of anhydrous chloroform was cooled in an ice bath under nitrogen. A solution of 235 ml. (393 g. = 2.56 mole) of phosphorous oxychloride in 400 ml. of chloroform was added at such a rate that the temperature did not rise above 15°. During the addition, which took place over a three-hour period, a viscous orange precipitate formed. This suspension was then stirred under nitrogen overnight. As much solvent as possible was removed at reduced pressure and the resulting red-brown paste was diluted with water and extracted with ether. The ether solutions were washed sequentially with water, 3N hydrochloric acid, water, 5 percent sodium hydroxide solution and water, and were dried over anhydrous sodium sulfate. Solvent removal at reduced pressure gave a dark oil which was distilled through a short Vigreux column to give 4-carboethoxy-3,5-dimethyl-isoxazole as a slightly cloudy, colorless liquid of b.p. 100°/11mm.

EXAMPLE 2

Preparation of 3,5-dimethyl-4-hydroxymethylisoxazole

A suspension of 100 g (2.63 moles) of lithium aluminum hydride in 2.5 liters of anhydrous ether was stirred under nitrogen as a solution of 272 g. (1.61 mole) of the 4-carboethoxy-3,5-dimethylisoxazole prepared in Example 1 above in 400 ml. of anhydrous ether was added at such a rate as to maintain a gentle reflux. The suspension was stirred at room temperature under nitrogen overnight, during which time an extremely gummy green-gray mass formed in the bottom of the flask. The mixture was cooled in an ice bath and hydrolyzed with saturated aqueous sodium sulfate solution. Anhydrous sodium sulfate was added to dry the ether solution. The salts were removed by filtration and washed carefully with ether and chloroform. Solvent removal from the filtrates, finally at 50°/0.1 mm., gave a white crystalline mass. This was triturated with hot ether and then cooled. Filtration gave 3,5-dimethyl-4-hydroxymethyl-isoxazole as white prisms, m.p. 76.5°/77.5°. Concentration of the mother liquors gave a second crop of prisms, m.p. 76.5°–78°.

EXAMPLE 3

Preparation of 4-chloromethyl-3,5-dimethylisoxazole

A solution at 36.3 ml. (60.0 g., 0.5 mole) of thionyl chloride in 50 ml. of methylene chloride was cooled in an ice bath under a very slight negative pressure (for fume removal). A solution of 40.0 g. (0.314 mole) of 3,5-dimethyl-4-hydroxymethylisoxazole in 75 ml. of methylene chloride was added over 2 ½ hours. The resulting solution was stirred at room temperature for 2.0 hours. The solvent was removed at reduced pressure and the residue was distilled to give the desired chloride as a pale yellow liquid, b.p. 91.5°–93°/15 mm.

EXAMPLE 4

Preparation of (3,5-dimethyl-4-isoxazolylmethyl)triphenylphosphonium chloride

A solution of 59.6 g. (0.402 mole) of 4-chloromethyl-3,5-dimethylisoxazole, prepared as described above, and 116 g. (0.44 mole) of triphenylphosphine in 1 liter of toluene was heated at reflux under nitrogen for 6 hours. The resulting suspension was cooled and filtered. The filtrate was heated at reflux for an additional 20 hours. The precipitate was again removed by filtration and the combined solids were washed well with ether and benzene. The solvent was removed from the filtrate and the residue was taken up in 150 ml. of fresh toluene and refluxed for an additional 18 hours. Filtration as before gave another small quantity of solid. The combined solids were crystallized from ethanol-ether to give the desired phsophonium salt as a cream-white solid, m.p. 313°–316°.

A sample from a similar preparation was crystallized again from ethanol-ether to give analytically pure material as small white prisms, m.p. 303°–305°. (The melting point of this compound is dependent on the rate of heating.)

Anal. Calcd. for $C_{24}H_{23}ClNOP$: C, 70.67; H, 5.68; Cl, 8.69; N, 3.44; O, 3.92; P, 7.60. Found: C, 70.73; H, 5.69; N, 3.55; Cl, 8.66.

EXAMPLE 5

Preparation of racemic 3,5-dimethyl-4-(3,4-dihydro-2H-pyran-2-ylvinyl) isoxazole 8.75 G. (0.20 mole) of 55 percent sodium hydride dispersion was washed under nitrogen with dry pentane to remove the mineral oil. To the flask was added 600 ml. of dimethylsulfoxide (dried over Linde 3A molecular sieves). The resulting suspension was carefully degassed, placed under nitrogen, and heated at 70°–75° for 1 hour. The gray-green solution was cooled to approximately 15° and 91.6 g. (0.20 mole) of (3,5-dimethyl-4-isoxazolylmethyl)triphenylphosphonium chloride, prepared as described in Example 4 above, was added in one portion. After approximately 5 minutes, a bright orange precipitate formed in the initially dark red solution. This suspension was stirred at room temperature for 45 minutes. To the mixture was then added, drop-wise via syringe, 25.0 g. (0.223 mole) of acrolein dimer (freshly distilled from and into hydroquinone) at such a rate that the temperature remained less than 30° (10–15 minutes with water bath cooling). The light orange-brown solution was stirred at room temperature for 20 minutes, and then at 60°–65° for 3 hours. (In some experiments, the mixture became very black during the heating period). The reaction mixture was cooled, poured onto ice, and slurried until all of the dark oil solidified. The suspension was filtered and the filter cake was washed well with pentane. The filtrates were extracted with pentane and the pentane solutions were washed with water and brine and dried over anhydrous sodium sulfate. Solvent removal gave a slightly orange oil which was distilled from a small quantity of anhydrous potassium carbonate to give the desired product as a colorless liquid, b.p. 83°–85°/0.1 mm. A similarly prepared sample of b.p. 77°–80°/0.5 mm. was submitted for analysis.

Anal. Calcd. for $C_{12}H_{15}NO_2$: C, 70.22; H, 7.37; N, 6.82; O, 15.59. Found: C, 70.45; H, 7.44; N, 6.60.

EXAMPLE 6

Preparation of racemic 7-(3,5-dimethyl-4-isoxazolyl)-5-hydroxy-$\Delta^6$-heptenoic acid lactone To a solution of 33.5 g. (0.163 mole) of 3,5-dimethyl-4-(3,4-dihydro-2H-pyran-2-ylvinyl) isoxazole, prepared as described in Example 5 above, in 400 ml. of dioxane, was added 400 ml. of 1N sulfuric acid and the cloudy solution, which soon cleared, was stirred at room temperature for 1 hour. The mixture was poured into 2 liters of saturated aqueous sodium bicarbonate solution and extracted well with ether. The ether extracts were washed with brine and dried over anhydrous sodium sulfate. Solvent removal gave a colorless oil, the infrared spectrum of which indicated that complete hydration of the enol ether had taken place. This material was taken up in 2 liters of benzene and placed under nitrogen. To the flask was added 400 g. of manganese dioxide and the resulting suspension was stirred at room temperature for 40 hours. The manganese dioxide was removed by filtration and carefully washed with fresh benzene. Solvent removal from the filtrate gave 23 g. of yellow solid. Two crystallizations of this material from benzene-ether gave the desired lactone as a cream-white powder, m.p. 90.0°–91.5°. A sample from a similar preparation was crystallized again from the same solvent pair to give analytically pure material as fine white needles, m.p. 91°–92.5°.

Anal. Calcd. for $C_{12}H_{15}NO_3$: C, 65.14; H, 6,83; O, 21.70; N, 6.33. Found: C, 64.93; H, 6.71; N, 6.06.

EXAMPLE 7

Preparation of racemic 7-(3,5-dimethyl-4-isoxazolyl)-5-hydroxyheptanoic acid lactone A. From racemic 7-(3,5-dimethyl-4-isoxazolyl)-5-hydroxy-$\Delta^6$-heptenoic acid lactone A mixture of 16.80 g. (76.0 mmoles) of racemic 7-(3,5-dimethyl-4-isoxazolyl)-5-hydroxy-$\Delta^6$-heptenoic acid lactone, 400 ml. of ethyl acetate, and 500 mg. of 10 percent palladium on carbon was hydrogenated at room temperature and atmospheric pressure. Uptake (1.25 × theoretical) was rapid and ceased after 2 hours. The catalyst was removed by filtration and washed with fresh ethyl acetate. Solvent removal gave a colorless oil which was crystallized from ether at −20° to give the desired product as white microprisms, m.p. 59°–62°. A small portion of a similarly prepared sample was crystallized again from ether to give white microprisms of m.p. 61°–62.5°, $\lambda_{max}^{ethanol}$ 220 m$\mu$ ($\epsilon = 5350$).

Anal. Calcd. for $C_{12}H_{17}NO_3$: C, 64.55; H, 7.68; O, 21.50; N, 6.27. Found: C, 64.59; H, 7.77; N, 6.12.

B. From 3,5-dimethyl-4-(3,4-dihydro-2H-pyran-2-ylvinyl) isoxazole

To a solution of 1.0 g. (4.88 mmoles) of 3,5-dimethyl-4-(3,4-dihydro-2H-pyran-2-ylvinyl) isoxazole, prepared as described in Example 5 above, in 10 ml. of ethanol was added 5 drops of 1N sulfuric acid. The solution was stirred at room temperature overnight, poured into excess saturated aqueous sodium bicarbonate solution, and extracted with ether. The ether extracts were washed with water and saturated brine and dried over anhydrous sodium sulfate. Solvent removal gave 1.25 g. of pale yellow liquid whose infrared spectrum indicated that formation of racemic 3,5-dimethyl-4-(6-ethoxytetrahydropyran-2-ylvinyl)isoxazole was complete. This material was taken up in 10 ml. of ethyl acetate. To this solution was added 25 mg. of 10 percent palladium on carbon and the resulting mixture was hydrogenated at room temperature and atmospheric pressure. After 2 hr., one equivalent of hydrogen had been consumed and uptake ceased. The catalyst was removed by filtration and washed with fresh ethyl acetate. Solvent removal from the filtrates gave 1.28 g. of racemic 3,5-dimethyl-4-(6-ethoxytetrahydropyran-2-ylethyl)-isoxazole as a colorless oil whose infrared spectrum indicated that the hydrogenation was complete. This crude acetal was taken up in 20 ml. of dioxane. To the flask was added 10 ml. of 1N sulfuric acid and the resulting solution was stirred at room temperature for 4 hr. It was then poured into excess saturated aqueous sodium bicarbonate solution and extracted with ether. The ether extracts were washed with saturated brine and dried over anhydrous sodium sulfate. Solvent removal gave racemic 3,5-dimethyl-4-(6-hydroxytetrahydropyran-2-ylethyl)-isoxazole as a viscous oil. The crude hemiketal was taken up in 25 ml. of 1,2-dichloroethane, degassed and placed under nitrogen. To the flask was added 7.5 g. of manganese dioxide and the resulting suspension was stirred at room temperature overnight. The manganese dioxide was removed by filtration and washed with fresh solvent. Solvent removal from the filtrates gave a pale yellow resin which was crystallized from ether at −20°C. to give the desired acetone as a white solid of m.p. 60°–62°. A similarly prepared sample was shown by its infrared and nmr spectra, mixture melting point, and thin layer chromatographic behavior to be identical with the material prepared as described above in part A.

C. Via Racemic 7-(3,5-dimethyl-4-isoxazolyl)-5-oxo-heptanoic acid

A solution of 3,5-dimethyl-4-(6-hydroxytetrahydropyran-2-ylethyl)-isoxazole, prepared as described in part B from 60.5 g. (0.294 mole) of racemic 3,5-dimethyl-4-(3,4-dihydro-2H-pyran-2-ylvinyl)-isoxazole, in 600 ml. of acetone was cooled in an ice bath as 400 ml. of Jones reagent was added dropwise over a 1.0 hr. period. The resulting suspension was stirred at room temperature overnight. Saturated sodium bisulfite solution was added to destroy the excess oxidizing agent and most of the acetone was removed at reduced pressure. The residue was diluted with water, saturated with sodium chloride, and extracted with ethyl acetate. The ethyl acetate solutions were washed with brine and then with excess saturated aqueous sodium bicarbonate solution. The sodium bicarbonate solutions were washed with ether, acidified with 3N hydrochloric acid, saturated with sodium chloride, and extracted with ethyl acetate. The ethyl acetate solutions were washed with brine and dried over anhydrous sodium sulfate. Solvent removal at reduced pressure gave a pale yellow resin. Crystallization of this material from ether gave two crops of racemic 7-(3,5-dimethyl-4-isoxazolyl)-5-oxo-heptanoic acid as a fine white powder, m.p. 61.5°–63.5°.

Anal. Calcd. for $C_{12}H_{17}NO_4$: C, 60.24; H, 7.16; N, 5.85. Found: C, 60.15; H, 7.29; N, 5.78.

A solution of the keto acid prepared above (41.2 g., 0.173 mole) in 600 ml. of isopropyl alcohol was placed under nitrogen. To this solution was carefully added 10.0 g. (0.296 mole) of sodium borohydride. After the initial vigorous reaction had subsided, the cloudy solution was heated at reflux overnight. A major portion of the solvent was then removed at reduced pressure. The residue was diluted with water, acidified with 1N hydrochloric acid, saturated with salt, and extracted with ether. The ether solutions were washed with brine and dried over anhydrous sodium sulfate. Solvent removal at reduced pressure gave racemic 7-(3,5-dimethyl-4-isoxazolyl)-5-hydroxyheptanoic acid as a cloudy colorless resin. This material was heated to 220°/0.3 mm., at which time a colorless liquid rapidly distilled. Crystallization from ether gave the desired lactone as white prisms, m.p. 61°–63°.

EXAMPLE 8

Racemic-3-[2-(3,5-dimethyl-4-isoxazolyl)ethyl]-6aβ-methyl-1,2,3,5,6,6a-hexahydrocyclopenta[f][1]benzopyran-7(8H)-one A. A solution of 10.0 g. (44.8 mmoles) of racemic 7-(3,5-dimethyl-4-isoxazolyl)-5-hydroxyheptanoic acid lactone, prepared as described in Example 7 above, in 150 ml. of freshly distilled tetrahydrofuran was cooled in a dry ice-isopropyl alcohol bath under nitrogen. A 25 per cent (weight/volume) solution of vinyl magnesium chloride in tetrahydrofuran (25 ml., 75 mmoles) was added via syringe at a rate such that the temperature remained at approximately −60°. The mixture was stirred at −70° for 15 min., and then carefully hydrolyzed with 5 ml. of methanol. It was then poured onto ice, 24 g. of ammonium chloride, and 8 ml. of acetic acid. The resulting solution was extracted with ether and the ether solutions were washed with water, saturated aqueous sodium bicarbonate solution, and saturated brine and dried over anhydrous sodium sulfate. After 10 minutes, 10 ml. of diethylamine was added to the ethereal solution of racemic 9-(3,5-dimethyl-4-isoxazolyl)-7-hydroxynon-1-en-3-one. Ten minutes later, solvent removal gave crude racemic 2-(2-diethylaminoethyl)-6-[2-(3,5-dimethyl-4-isoxazolyl)ethyl]tetrahydropyran-2-ol as a light yellow oil. This material was taken up in ether and extracted with a total of 100 ml. of 1N hydrochloric acid followed by 25 ml. of water. The aqueous solutions were washed with ether and then placed under a layer of ether in an ice bath. The solution was made basic with 3N sodium hydroxide and then extracted with ether. The ether extracts were washed with water and saturated brine and dried over anhydrous sodium sulfate. Solvent removal gave the Mannich base as a pale yellow oil.

A solution of 5.3 g. (47.2 mmoles) of 2-methylcyclopentane-1,3-dione in 150 ml. of toluene and 50 ml. of acetic acid was carefully degassed, placed under nitrogen and heated at reflux for 5 minutes. A solution of the Mannich base prepared above in 50 ml. of toluene was added and refluxing was continued for 2 hr. The cooled solution was washed with water, saturated aqueous sodium bicarbonate solution and saturated brine and dried over anhydrous sodium sulfate. Solvent removal gave a reddish-orange gum which was filtered through 150 g. of Woelm neutral alumina, activity grade III. Elution with benzene brought off a light pink band followed by a yellow band. Solvent removal from the eluent gave the desired dienol ether as a light orange crystalline solid.

A sample of this product was crystallized from ether-hexane and then from ether at −20° to give analytically pure racemic 3-[2-(3,5-dimethyl-4-isoxazolyl)ethyl]-6aβ-methyl-1,2,3,5,6,6a-hexahydrocyclopenta[f][1]benzopyran-7(8H)-one as light yellow prisms of m.p. 113°–116°.

Anal. Calcd. for $C_{20}H_{25}NO_3$: C, 73.36; H, 7.70; N, 4.28; O, 14.66. Found: C, 73.64; H, 7.72; N, 4.57.

B. To a solution of 20.0 g. (89.6 mmoles) of racemic 7-(3,5-dimethyl-4-isoxazolyl)-5-hydroxy heptanoic acid lactone, prepared as described in Example 7 above, in 100 ml. of dry toluene, which had been cooled to −70°C. under nitrogen, was added 95 ml. of a 20% solution of diisobutylaluminum hydride dropwise over a period of ¾ hour. The mixture was stirred 1 hour at −70°C., and then hydrolyzed in the cold with 80 ml. of 6 N sulfuric acid. After the solution had warmed to room temperature, the layers were separated and the organic solutions were washed with water, saturated aqueous sodium bicarbonate solution and brine and dried over anhydrous sodium sulfate. Solvent removal at reduced pressure gave racemic 3,5-dimethyl-4-(6-hydroxytetrahydropyran-2-ylethyl)isoxazole as 18.1 g. of colorless viscous oil.

In a previously dried flask, 200 ml. of a 1 M solution of vinyl magnesium chloride in tetrahydrofuran was stirred at room temperature as a solution of the hemiacetal prepared above (alternatively, hemiacetal prepared as described in Example 7 may be used) in 50 ml. of tetrahydrofuran was added at such a rate that the temperature remained less than 35°. The mixture was stirred at room temperature overnight and then hydrolyzed by pouring onto ice and ammonium chloride. Extraction with ether, washing the ether solutions with brine, drying over anhydrous sodium sulfate, and solvent removal gave racemic 9-(3,5-dimethyl-4-isoxazolyl)-non-1-en-3,7-diol as a viscous colorless resin.

To a solution of the diol prepared above and 0.25 g. of hydroquinone in 600 ml. of 1,2-dichloroethane was added 120 g. of manganese dioxide. The resulting slurry was stirred 6 hours at room temperature before the manganese dioxide was removed by filtration. The filter cake was washed well with fresh 1,2-dichloroethane and the combined filtrates were concentrated to 500 ml. To this solution of racemic 9-(3,5-dimethyl-4-isoxazolyl)-7-hydroxy non-1-en-3-one was added 10 ml. of diethylamine. After ½ hour, solvent removal at reduced pressure gave crude racemic 2-(2-diethylaminoethyl)-6-[2-(3,5-dimethyl-4-isoxazolyl)ethyl] tetrahydropyran-2-ol as a light yellow oil. This material was taken up in ether and extracted with a total of 100 ml. of 1N hydrochloric acid followed by 25 ml. of water. The aqueous solutions were washed with ether and then placed under a layer of ether in an ice bath. The solution was made basic with 3N sodium hydroxide and then extracted with ether. The ether extracts were washed with water and saturated brine and dried over anhydrous sodium sulfate. Solvent removal gave the Mannich base as a pale yellow oil.

A solution of 5.3 g. (47.2 mmoles) of 2-methylcyclopentane-1,3-dione in 150 ml. of toluene and 50 ml. of acetic acid was carefully degassed, placed under nitrogen and heated at reflux for 5 minutes. A solution of the Mannich base prepared above in 50 ml. of toluene was added and refluxing was continued for 2 hours. The cooled solution was washed with water, saturated aqueous sodium bicarbonate solution and saturated brine and dried over anhydrous sodium sulfate. Solvent removal gave a reddish-orange gum which was filtered through 150 g. of Woelm neutral alumina, activity grade III. Elution with benzene gave dienol ether spectrally identical with the material prepared in part A as a pale orange solid.

EXAMPLE 9

Preparation of racemic
trans-anti-6-[(3,5-dimethyl-4-isoxazolyl)methyl]-3a-methyl-1,2,3a,4,5,9,9a,9b-octahydro-3H-benz(e)indene-3,7(8H)-dione A suspension of 1.60 g. (41 mmoles) of lithium aluminum hydride in 150 ml. of freshly distilled tetrahydrofuran was cooled under nitrogen in an ice bath as a solution of 12.0 g. of the dienol ether racemic 3-[2-(3,5-dimethyl-4-isoxazolyl) ethyl]-6a$\beta$-methyl-1,2,3,5,6,6a-hexahydrocyclopenta[f][1]benzopyran-7-(8H)-one, the preparation of which is described in Example 8, in 50 ml. of tetrahydroguran was added over 10 minutes. The suspension was stirred at 0° for another 10 minutes and then at room temperature for ½ hr. The mixture was cooled again in an ice bath, carefully hydrolyzed with saturated aqueous sodium sulfate solution, and dried over anhydrous sodium sulfate. The salts were removed by filtration and washed with fresh tetrahydrofuran and chloroform. Solvent removal from the filtrates gave a cream-white solid. Normally the hydroxy dienol ether thus obtained was used without further purification. However, the material from one experiment was crystallized from ether-tetrahydrofuran and then from tetrahydrofuran to give analytically pure racemic 3-[2-(3,5-dimethyl-4-isoxazolyl)ethyl]-6a$\beta$-methyl-1,2,3,5,6,6a,7,8-octahydrocyclopenta[f][1]benzopyran-7$\beta$-ol, as a cream-white crystalline powder, m.p. 158.5°–165°.

Anal. Calcd. for $C_{20}H_{27}NO_3$: C, 72.92; H, 8.26; O, 14.57; N, 4.25. Found: C, 73.22; H, 8.26; N, 4.03.

The crude hydroxy dienol ether prepared above was dissolved in 350 ml. of freshly distilled tetrahydrofuran. To this solution was added 750 mg. of a 5 per cent palladium on carbon catalyst and the resulting mixture was hydrogenated at atmospheric pressure and room temperature. Uptake of one equivalent of hydrogen took 4 hours. The catalyst was removed by filtration and washed with fresh tetrahydrofuran. Solvent removal gave racemic trans-3-[2-(3,5-dimethyl-4-isoxazolyl)ethyl]-6a-methyl-1,2,3,5,6,6a,7,8,9,9a-decahydrocyclopenta[f][1]benzopyran-7$\beta$-ol as a pale green resin.

A solution of the hydroxy enol ether trans-3-[2-(3,5-dimethyl-4-isoxazolyl)ethyl]-6a-methyl-1,2,3,5,6,6a,7,8,9,9a-decahydrocyclopenta[f][1]benzopyran-7$\beta$-ol prepared above in 250 ml. of acetone was stirred at room temperature with 125 ml. of 1N sulfuric acid for 1½ hr., during which time the solution became light pink in color. This solution was carefully poured into excess saturated aqueous sodium bicarbonate solution and extracted with chloroform. The chloroform solutions were washed with brine and dried over anhydrous sodium sulfate. Solvent removal gave racemic trans-3-[2-(3,5-dimethyl-4-isoxazolyl)ethyl]-6a-methyl-perhydrocyclopenta[f][1]benzopyran-4a,7$\beta$-diol as a yellow resin. The infrared spectrum of this sample showed that complete hydration of the enol ether had occurred.

A solution of the hemiketal trans-3-[2-(3,5-dimethyl-4-isoxazolyl)ethyl]-6a-methyl-perhydrocyclopenta[f][1]benzopyran-4a,7$\beta$-diol in 400 ml. of acetone was cooled in an ice bath as a solution of 20 g. (0.20 mole) of chromium trioxide in 100 ml. of 6N sulfuric acid was added dropwise over ½ hr. The mixture was stirred at 0° for another ½ hr., and then at room temperature for 1½ hr. It was then diluted with water and extracted with benzene. The benzene extracts were washed with water, saturated aqueous sodium bicarbonate solution and saturated brine and dried over anhydrous sodium sulfate. Solvent removal gave racemic trans-4-[3-oxo-5(3,5-dimethyl-4-isoxazolyl)pentyl]-1a-methyl-perhydroindan-1,5-dione as a pale yellow resin.

The crude trione trans-4-[3-oxo-5-(3,5-dimethyl-4-isoxazolyl)pentyl]-1a-methyl-perhydroindan-1,5-dione was dissolved in 100 ml. of methanol, carefully degassed and placed under nitrogen. To the solution was added 1 g. of potassium hydroxide and the resulting black mixture was heated at reflux under nitrogen for 1½ hr. The cooled solution was diluted with water and extracted with benzene. The benzene extracts were washed with water and saturated brine and dried over anhydrous sodium sulfate. Solvent removal gave 8.33 g. of an orange solid which was filtered through 150 g. of Woelm neutral alumina, activity grade I. Elution with 3:1 benzene:ether slowly brought off the desired isoxazole ene-dione (In later experiments, the use of activity grade III neutral alumina and elution with benzene was found to be superior). Crystallization from benzene-hexane gave the desired product as white prisms, m.p. 141°-143.5°. A sample from a similar preparation was crystallized again from benzene-hexane to give an analytically pure material, m.p. 141.5°-143.5°.

Anal. Calcd. for $C_{20}H_{25}NO_3$: C, 73.36; H, 7.70; N, 4.28; O, 14.66. Found: C, 73.39; H, 7.64; N, 4.38.

EXAMPLE 10

Preparation of racemic 19-nor-Androst-4-en-3,17-dione

A mixture of 1.00 g. (3.06 mmoles) of the isoxazole ene-dione racemic trans-anti-6-(3,5-dimethyl-4-isoxazolylmethyl)-3a-methyl-1,2,3a,4,5,9,9a,9b-octahydro-3H-benz(e)indene-3,7(8H)-dione, prepared as described in Example 9 above, 60 mg. of 10 per cent palladium on carbon, and 100 ml. of 3:1 ethanol triethylamine was hydrogenated at atmospheric pressure and room temperature. Within 1 hour, one equivalent of hydrogen had been taken up and uptake had ceased. Normally, the product was not isolated. In one case however, the catalyst was removed by filtration and after solvent removal the crude product was crystallized from benzene-hexane to give pure racemic trans-anti-trans-anti-6-[(3,5-dimethyl-4-isoxazolyl)methyl]-3a-methyl-3a,4,5,5a,8,9,9a,9b-octahydro-1H-benz[e]inden-3,7(2H,6H)-dione as white prisms of m.p. 137.5°-139.5°.

Anal. Calcd. for $C_{20}H_{27}NO_3$: C, 72.92; H, 8.26; N, 4.25; O, 14.57. Found: C, 72.89; H, 7.93; N, 4.22, 4.34.

To the hydrogenation mixture described above was added 10 ml. of a 1N potassium hydroxide in ethanol solution which had been carefully degassed and placed under nitrogen. After 1½ hr., a second equivalent of hydrogen had been taken up. The catalyst was removed by filtration and washed with fresh ethanol. Solvent removal from the filtrates gave the vinylogous amide as a pale yellow resin which was immediately taken up in 25 ml. of butyl alcohol. This solution was carefully degassed and placed under nitrogen. To the flask was added 100 ml. of a previously degassed 20 per cent aqueous potassium hydroxide solution. The resulting two phase mixture was heated at reflux under nitrogen for 20 hours. The cooled solution was diluted with water and extracted with ether. The ether extracts were washed with water, 1N hydrochloric acid, water, and saturated brine and dried over anhydrous sodium sulfate. Solvent removal gave 690 mg. of yellow crystalline solid. This material was chromatographed on 100 g. of Merck silica gel. Elution with 7:2 and 7:3 benzene:ether mixtures gave a light yellow solid which was homogenous by thin layer chromatography. Crystallization from acetone isopropyl ether gave racemic 19-nor-androst-4-ene-3,17-dione as a very pale yellow solid, m.p. 156.5°-158.5°.

EXAMPLE 11

Preparation of trans-anti-trans-anti-6-[(3,5-dimethyl-4-isoxazolyl)methyl]-3,3,7,7,-bis(ethylenedioxy)-3a-methyl-perhydro-1H-benz[e]indene A solution of 654 mg. (2.0 mmoles) of the isoxazole ene dione racemic trans-anti-6-(3,5-dimethyl-4-isoxazolylmethyl)-3a-methyl-1,2,3a,4,5,9,9a,9b-octahydro-3H-benz(e)indene-3,7(8H)-dione prepared as described above, in 50 ml. of 3:1 ethanol:triethylamine containing 60 mg. of 10 per cent palladium on carbon was hydrogenated at atmospheric pressure and room temperature. After 1.0 hr. uptake (1.0 equivalent) had ceased. The catalyst was removed by filtration and washed with fresh ethanol. Solvent removal from the filtrates gave the isoxazole dione, racemic trans-anti-trans-anti-6-[(3,5-dimethyl-4-isoxazolyl)methyl]-3a-methyl-3a,4,5,5a,8,9,9a,9b-octahydro-1H-benz[e]inden-3,7(2H,6H)dione as a colorless foam. This material was taken up in 15 ml. of ethylene glycol and 50 ml. of benzene, degassed, and placed under nitrogen. To the solution was added 400 mg. of p-toluenesulfonic acid monohydrate and the resulting mixture was heated at reflux under nitrogen, with azeotropic removal of water, for 21 hr. After 2 hr., Linde 3A molecular sieves were placed in the Dean-Stark trap. The pale pink solution was extracted with excess saturated aqueous sodium bicarbonate solution and brine and dried over anhydrous sodium sulfate. Solvent removal at reduced pressure gave the crude isoxazole diketal as a very pale yellow resin.

Pure isoxazole diketal, racemic trans-anti-trans-anti-6-[(3,5-dimethyl-4-isoxazolyl)methyl]-3,3,7,7-bis(ethylenedioxy)-3a-methyl-perhydro-1H-benz[e]indene, was obtained from one such reaction by crystallization of the crude material from ether at −20°C.

Anal. Calcd. for $C_{24}H_{35}NO_5$: C, 69.03; H, 8.45; N, 3.35; O, 19.16. Found: C, 69.34; H, 8.64; N, 3.35.

EXAMPLE 12

Preparation of racemic trans-anti-trans-anti-3,3,7,7-bis(ethylenedioxy)3a-methyl-6-(3-oxobutyl)perhydro-1H-benz[e]indene The crude noncrystalline isoxazole diketal racemic trans-anti-trans-anti-6-[(3,5-dimethyl-4-isoxazolyl)methyl]-3,3,7,7-bis(ethylenedioxy)3a-methyl-perhydro-1H-benz[e]indene whose preparation is described in Example 11 above was dissolved in 40 ml. of ethanol containing 1.5 g. of potassium hydroxide and 80 mg. of 10 per cent palladium on carbon. The resulting solution was hydrogenated at atmospheric pressure and room temperature, under which conditions uptake of one equivalent of hydrogen took 4 hr. The catalyst was removed by filtration and washed with fresh ethanol. The solvent was removed from the filtrates until a residue of approximately 10 ml. remained. This solution of the vinylogous amide was degassed and placed under nitrogen. A previously degassed 20 per cent aqueous potassium hydroxide solution (50 ml.) was added and the resulting mixture was heated at reflux under nitrogen for 18 hr. The cooled solution was diluted with water and extracted with benzene. The benzene solutions were washed with brine and dried over anhydrous sodium sulfate. Solvent removal gave the desired oxo diketal as a pale yellow resin.

Crystallization of the product of a similar preparation four times from ether yielded analytically pure racemic trans-anti-trans-anti-3,3,7,7-bis(ethylenedioxy)-3a-methyl-b-(3-oxobutyl)perhydro-1H-benz[e]indene as fine white needles, m.p. 126.5°–128°. This layer chromatography (1:1 benzene-ethyl acetate) showed only one spot.

Anal. Calcd. for $C_{22}H_{34}O_5$: C, 69.81; H, 9.05; O, 21.14. Found: C, 70.11; H, 8.99.

EXAMPLE 13

Preparation of racemic 19-nor-Androst-4-en-3,17-dione

The crude keto diketal, racemic trans-anti-trans-anti-3,3,7,7-bis(ethylenedioxy)-3a-methyl-6-(3-oxobutyl)-perhydro-1H-benz[e]indene whose preparation is described in Example 12 above, was suspended in 30 ml. of methanol, degassed, and placed under nitrogen. To the flask was added 3 ml. of 4N hydrochloric acid and the resulting solution was heated at reflux under nitrogen for 3 hr. The cooled mixture was diluted with water and extracted with benzene. The benzene solutions were washed with saturated aqueous sodium bicarbonate solution and brine and dried over anhydrous sodium sulfate. Thin layer chromatography (1:1 benzene-ethyl acetate) of the solution showed only one very faint spot in addition to that corresponding to authentic 19-nor-androst-4-en-3,17-dione. Solvent removal gave pale tan crystals which were chromatographed on 25 g. of Silica Gel. The material eluted with 9:1 and 8:2 benzene-ether mixtures was triturated with refluxing isopropyl ether and then cooled to −20° to give racemic 19-nor-androst-4-en-3,17-dione as white prisms, m.p. 157°–159.5°.

EXAMPLE 14

Preparation of racemic trans-anti-6-[(3,5-dimethyl-4-isoxazolyl)methyl]-3,3,7,7-bis(ethylenedioxy)-3a-methyl-2,3,3a,4,6,7,8,9-,9a,9b-decahydro-1H-benz[e]indene A solution of 981 mg. (3.0 mmoles) of the isoxazole ene dione, racemic trans-anti-6-(3,5-dimethyl- 4-isoxazolylmethyl)-3a-methyl-1,2,3a,4,5,9,9a,9b,-octahydro-3H-benz(e)indene-3,7(8H)-dione, 600 mg. of p-toluenesulfonic acid monohydrate and 15 ml. of ethylene glycol in 50 ml. of benzene was heated at reflux under nitrogen, with azeotropic removal of water, for 23 hr. After 2.0 hr., Linde 3A molecular sieves were placed in the Dean-Stark trap. The solution was cooled, washed with excess saturated aqueous sodium bicarbonate solution and brine and dried over anhydrous sodium sulfate. Solvent removal at reduced pressure gave a colorless resin which was crystallized from ether-hexane to give the desired product, racemic trans-anti-6-[(3,5-dimethyl-4-isoxazolyl)methyl]-3,3,7,7-bis (ethylenedioxy)-3a-methyl-2,3,3a,4,6,7,8,9,9a,9b-decahydro-1H-benz[e]indene as a white crystalline solid, m.p. 120°–127°. A sample from a similar preparation was crystallized again from ether-hexane to give the analytically pure diketal as colorless microprisms of m.p. 127°–129°.

Anal. Calcd. for $C_{24}H_{33}NO_5$: C, 69.37; H, 8.01; N, 3.37; O, 19.25. Found: C, 69.25; H, 8.25; N, 3.36.

EXAMPLE 15

Preparation of racemic trans-anti-3,3,7,7-bis(ethylenedioxy)-3a-methyl-6-(3-oxobutyl)-2,3,3a,4,6,7,8,9,9a, 9b-decahydro-1H-benz[e]indene A solution of 830 mg. (2.0 mmoles) of the isoxazole ene diketal, racemic trans-anti-6-[(3,5-dimethyl-4-isoxazolyl)methyl]-3,3,7,7-bis(ethylenedioxy)-3a-methyl-2,3,3a,4,6,7,8,9,9a,9b-decahydro-1H-benz[e]indene prepared as described in Example 14 above, in 40 ml. of ethanol containing 2.0 g. of potassium hydroxide and 80 mg. of 10 per cent palladium on carbon was hydrogenated at atmospheric pressure and room temperature. Uptake (1.0 equivalent) of hydrogen ceased after 6 hr. The catalyst was removed by filtration and washed with fresh ethanol. The solvent was removed from the filtrate until a residue of 10 ml. remained. This solution of the vinylogous amide was degassed and placed under nitrogen. A previously degassed solution (50 ml.) of 20 per cent aqueous potassium hydroxide was added and the resulting mixture was heated at reflux for 18 hr. The reaction mixture was then diluted with water and extracted with benzene. The benzene solutions were washed with brine and dried over anhydrous sodium sulfate. Solvent removal gave a pale yellow resin which was homogenous to thin layer chromatography..

Crystallization of a sample from a similar preparation three times from isopropyl ether gave racemic trans-anti-3,3,7,7-bis(ethylenedioxy)-3a-methyl-6-(3-oxobutyl)-2,3,3a,4,6,7,8,9,9a,9b-decahydro-1H-benz[e]indene as cream-white prisms, m.p. 80.0°–83.5°.

Anal. Calcd. for $C_{22}H_{32}O_5$: C, 70.18; H, 8.57; O, 21.25. Found: C, 70.85, 70.69; H, 8.68, 8.51.

EXAMPLE 16

Preparation of racemic trans-anti-3a-methyl-6-(3-oxobutyl)-3a,4,5,9,9a, 9b-hexahydro-1H-benz[e]indene-3,7(2H, 8H)-dione The crude keto ene diketal, racemic trans-anti-3,3,7,7-bis-(ethylenedioxy)-3a-methyl-6-(3-oxobutyl)-2,3,3a,4,6,7,8,9,9a,9b-decahydro-1H-benz[e]indene, whose preparation is described in Example 15 above, was dissolved in 30 ml. of 1:1 water-acetic acid, degassed, placed uner nitrogen, and heated at 90°–100° for 1½ hr. The pale yellow solution was then cooled, diluted with water, and extracted with benzene. The benzene solutions were washed with saturated aqueous sodium bicarbonate solution and brine and dried over anhydrous sodium sulfate. Solvent removal at reduced pressure gave 650 mg. of pale yelllow resin. This material was crystallized three times from ether to give the pure trione, racemic trans-anti-3a-methyl-6-(3-oxobutyl)-3a,4,5,9,9a,9b-hexahydro-1H-benz[e]inden-3,7(2H,8H)-dione as pale yellow prisms, m.p. 101.5°–103°.

Anal. Calcd. for $C_{18}H_{24}O_3$: C, 74.97; H, 8.39; O, 16.64. Found: C, 74.80, H, 8.54.

EXAMPLE 17

Preparation of (−) 7-(3,5-dimethyl-4-isoxazolyl)-5-hydroxy-heptanoic acid lactone A solution of 5.0 g. (22.4 mmoles) of racemic 7-(3,5-dimethyl-4-isoxazolyl)-5-hydroxyheptanoic acid lactone, 7.80 g. (50 mmoles) of (−) menthol and 0.1 g. of p-toluenesulfonic acid in 100 ml. of benzene was heated at reflux under nitrogen for 16 hours. The solution was cooled and washed with saturated aqueous sodium bicarbonate solution and brine and dried over anhydrous sodium sulfate. Solvent removal at reduced pressure gave a mixture of diastereomeric esters as a pale yellow oil. The desired R ester (the absolute configuration was determined by conversion of this material to (+) 19-nor-androst-4-en-3,17-dione) was obtained by preparative vapor phase chromatography. A solution of 2.10 g. of this ester in 50 ml. of 3N-aqueous potassium hydroxide was heated at reflux under nitrogen for 18 hours. The solution was cooled, extracted with ether, acidified with 3N-hydrochloric acid, saturated with sodium chloride and extracted with methylene chloride. The methylene chloride solutions were washed with brine and dried over anhydrous sodium sulfate. Solvent removal gave a cloudy colorless resin. This crude product was heated to 200°C. at 0.2 mm., at which time the desired R-lactone, (−) 7-(3,5-dimethyl-4-isoxazolyl)-5-hydroxy-heptanoic acid lactone distilled as a colorless liquid.

EXAMPLE 18

(−) 2-(2-(−)-α-phenethylaminoethyl)-6-[2-(3,5-dimethyl-4-isoxazolyl)ethyl]-tetrahydropyran-2-ol oxalate A solution of 22.3 g. (0.1 mole) of racemic 7-(3,5-dimethyl-4-isoxazolyl)-5-hydroxy heptanoic acid lactone, prepared as described in Example 7, in 330 ml. of dry tetrahydrofuran was cooled in a dry ice-acetone bath under nitrogen as 85 ml. of a 2 M solution of vinyl magnesium chloride in tetrahydrofuran was added at such a rate as to keep the temperature at −50° to −55° (15 min.). Stirring was continued for 30 min. before the solution was hydrolyzed by the careful addition of 11 ml. of methanol. The solution was poured onto ice, 53 g. of ammonium chloride and 16 ml. of acetic acid and extracted with ether. The ether solutions were washed with saturated aqueous sodium bicarbonate solution and brine and dried over anhydrous sodium sulfate. Solvent removal gave 24.8 g. of crude 9-(3,5-dimethyl-4-isoxazolyl)-7-hydroxy-non-1-en-3-one as a yellow oil. This crude vinyl ketone was dissolved in 150 ml. of dry benzene. To this solution was added 8.56 g. of (−) α-phenethylamine and the resulting mixture was stirred under nitrogen at 45° for 2.0 hr. The mixture was evaporated to dryness to give the crude Mannich base as 43.2 g. of yellow oil. This crude Mannich base was taken up in 150 ml. of ether and mixed with a solution of 8.5 g. of oxalic acid in 100 ml. of ether. The oil which separated was removed and washed with ether. The oil was crystallized from acetonebenzene to give the desired oxalate as a white solid, m.p. 111°–114°. Three further crystallizations from methanol-ether gave analytically pure (−) 2-(2-(−)-α-phenethylaminoethyl)-6-[2-(3,5-dimethyl-4-isoxazolyl)ethyl]tetrahydropyran-2-ol oxalate as a white powder, m.p. 118°–120°.

Anal. Calcd. for $C_{24}H_{34}N_2O_7$: C, 62.32; H, 7.41; N, 6.06; O, 24.21. Found: C, 62.26; H, 7.38.

EXAMPLE 19

(−) 3-[2-(3,5-Dimethyl-4-isoxazolyl)ethyl]-6aβ-methyl-1,2,3,5,6,6a-hexahydrocyclopenta[f][1]benzopyran-7(8H)-one A solution of 84.0 mg. of 2-methyl-cyclopentane-1,3-dione in 5 ml. of toluene, 2 ml. of 95% acetic acid and 1 ml. of pyridine was carefully degassed, placed under nitrogen, and heated at reflux 1 min. To the solution was added 231 mg. of (−) 2-(2-(−) α-phenethylaminoethyl)-6-[2-(3,5-dimethyl-4-isoxazolyl)ethyl]-tetrahydropyran-2-ol oxalate, prepared as described in Example 18, and the resulting mixture was heated at reflux for 3½ hr., the last ½ hr. with azeotropic removal of water. The cooled solution was diluted with benzene and washed with brine, saturated aqueous sodium bicarbonate solution and brine and dried over anhydrous sodium sulfate. Solvent removal gave a brown oil which was chromatographed on 20 g. of activity III neutral alumina. Elution with hexane-benzene mixtures gave the desired dienol ether as pale yellow needles, m.p. 85°–88°. Crystallization of this material from isopropyl ether gave analytically pure (−) 3-[2-(3,5-dimethyl-4-isoxazolyl)ethyl]-6aβ-methyl-1,2,3,5,6,6a-hexahydrocyclopenta[f][1]benzopyran-7(8H)-one as pale yellow needles, m.p. 90°–91.5°.

Anal. Calcd. for $C_{20}H_{25}NO_3$: C, 73.36; H, 7.70; N, 4.28; O, 14.66. Found: C, 73.29; H, 7.74; N, 4.15.

EXAMPLE 20

(+) trans-anti-6-[(3,5-Dimethyl-4-isoxazolyl)methyl]-3a-methyl-1,2,3a,4,5,9,9a,9b-octahydro-3H-benz[e]indene-3,7-(8H)-dione A solution of 250 mg. of lithium aluminum hydride in 25 ml. of freshly distilled tetrahydrofuran was cooled in an ice bath under nitrogen as a solution of 789 mg. of (−) 3-[2-(3,5-dimethyl-4-isoxazolyl)ethyl]-6aβ-methyl-1,2,3,5,6,6a-hexahydrocyclopenta-[f][1]benzopyran-7(8H)-one, prepared as described in Example 19, in 5 ml. of tetrahydrofuran was added over 5 min. The mixture was stirred at 0° for 15 min. and then without cooling for an additional 30 min. The reaction mixture was cautiously hydrolyzed at 0° with saturated aqueous sodium sulfate solution, dried over anhydrous sodium sulfate, and filtered. Solvent removal from the filtrates gave crude 3-[2-(3,5-dimethyl-4-isoxazolyl)ethyl]-6aβ-methyl-1,2,3,5,6,6a,7,8-octahydrocyclopenta[f][1]benzopyran-7β-ol as a pale orange glass.

The crude alcohol was taken up in 20 ml. of tetrahydrofuran. To this solution was added 100 mg. of a 5 per cent palladium on carbon catalyst and the mixture was hydrogenated at atmospheric pressure and room temperature. The uptake of one equivalent of hydrogen took 15 hr. Removal of the catalyst by filtration, followed by solvent removal at reduced pressure gave trans-3-[2-(3,5-dimethyl-4-isoxazolyl)ethyl]-6a-methyl-1,2,3,5,6,6a,7,8,9,9a-decahydrocyclopenta[f][1]benzopyran-7β-ol as a pale orange resin. This crude enol ether was taken up in 20 ml. of acetone, degassed, and placed under nitrogen. To this solution was added 10 ml. of 1N sulfuric acid and the resulting mixture was stirred at room temperature for 1½ hr., poured into saturated aqueous sodium bicarbonate solution and extracted with chloroform. The chloroform solutions were washed with saturated aqueous sodium bicarbonate solution and saturated brine and dried over anhydrous sodium sulfate. Solvent removal gave the crude hemiketal, trans-3-[2-(3,5-dimethyl-4-isoxazolyl)ethyl]-6a-methyl-perhydrocyclopenta[f][1]benzopyran-4a,7b-diol as an orangish-colored foam.

The crude hemiketal was dissolved in 20 ml. of acetone and cooled in an ice bath as a solution of 1.5 g. of chromium trioxide in 7.5 ml. of 6N sulfuric acid was added over 20 min. The resulting suspension was stirred at 0° for 40 min. and then for an additional 1½ hr. without cooling. It was then poured into water and extracted with benzene. The benzene solutions were washed with water, saturated aqueous sodium bicarbonate solution, and brine and dried over anhydrous sodium sulfate. Solvent removal gave crude trans-4-[3-oxo-5(3,5-dimethyl-4-isoxazolyl) pentyl]1a-methyl-perhydroindan-1,5-dione as a pale orange resin. This material was taken up in 20 ml. of methanol, degassed and placed under nitrogen. To the flask was added 200 mg. of sodium hydroxide and the resulting dark solution was heated at reflux 2.0 hr., cooled, diluted with water, and extracted with benzene. The benzene solutions were washed with brine and dried over anhydrous sodium sulfate. Solvent removal gave the crude isoxazole ene dione which was chromatographed on neutral alumina, activity III. The material eluted with a 95:5 benzene-ether mixture was crystallized from isopropyl ether to give pure (+) trans-anti-6-[(3,5-dimethyl-4-isoxazolyl)methyl]-3a-methyl-1,2,3a,4,5,9-,9a,9b-octahydro-3H-benz[e]indene-3,7(8H)-dione as colorless needles, m.p. 85°–87.5°.

EXAMPLE 21

Preparation of (+) trans-anti-6-[(3,5-dimethyl-4-isoxazolyl)methyl]-3a-methyl-3β-tertiary butoxy-1,2,3,3a,4,5,8,9,9a,9b-decahydro-7H-benz[e]indene-7-one In a dry flask, 520 mg. of 55% sodium hydride dispersion was washed with pentane to remove the mineral oil. The sodium hydride was suspended in 100 ml. of freshly distilled 1,2-dimethoxyethane and 2.76 g. of (+) trans-anti-3a-methyl-3β-tertiary butoxy-1,2,3,3a,4,5,8,9,9a,9b-decahydro-7H-benz[e]indene-7-one was added to the suspension. The mixture was heated at reflux under nitrogen for 1.0 hr. A solution of 1.75 g. of 4-chloromethyl-3,5-dimethylisoxazole in 20 ml. of 1,2-dimethoxyethane was then added at reflux over a period of 4½ hr. The suspension was heated at reflux an additional 1½ hr., cooled, diluted with water, and extracted with benzene. The benzene solutions were washed with brine and dried over anhydrous sodium sulfate. The orange resin obtained upon solvent removal was chromatographed on 200 g. of silica gel. The material obtained by elution with 95:5 and 90:10 benzene-ether mixtures was crystallized from ether-hexane to give analytically pure (+) trans-anti-6-[(3,5-dimethyl-4-isoxazolyl)methyl]-3a-methyl-3β-tertiary butoxy-1,2,3,3a,4,5,8,9,9a,9b-decahydro-7H-benz[e]indene-7-one, m.p. 125.5°–126.5°.

Anal. Calcd. for $C_{24}H_{35}N_1O_3$: C, 74.76; H, 9.15; N, 3.63; O, 12.45. Found: C, 74.88; H, 9.38; N, 4.67.

EXAMPLE 22

Preparation of (−) trans-anti-6-[(3,5-dimethyl-4-isoxazolyl)methyl]-3a-methyl-3β-hydroxy-1,2,3,3a,4,5,8,9,9a,9b-decahydro-7H-benz[e]indene-7-one A solution of 1.159 g. of (+) trans-anti-6-[(3,5-dimethyl-4-isoxazolyl)methyl]-3a-methyl-3β-tertiary butoxy-1,2,3,3a,4,5,8,9,9a,9b-decahydro-7H-benz[e]indene-7-one, prepared as described in Example 21, and 1.1 g. of p-toluenesulfonic acid monohydrate in 100 ml. of benzene was degassed, placed under nitrogen and heated at reflux for 1.0 hr. The cooled solution was washed with saturated aqueous sodium bicarbonate solution and brine and dried over anhydrous sodium sulfate. Solvent removal gave a yellowish resin which was crystallized from isopropyl ether to give the desired alcohol as fine white needles, m.p. 127°–127.5°.

Anal. Calcd. $C_{20}H_{27}N_1O_3$: C, 72.92; H, 8.26; N, 4.25; O, 14.57. Found: C, 73.25; H, 8.49; N, 4.16.

EXAMPLE 23

Preparation of (+) trans-anti-6-[(3,5-dimethyl-4-isoxazolyl)methyl]-3a-methyl-1,2,3a,4,5,9,9a,9b-octahydro-3H-benz[e]indene-3,7(8H)-dione A solution of 415 mg. of (−) trans-anti-6-[(3,5-dimethyl-4-isoxazolyl)methyl]-3a-methyl-3β-hydroxy-1,2,3,3a,4,5,8,9,9a,9b-decahydro-7H-benz[e]indene-7-one, prepared as described in Example 22, in 25 ml. of acetone was cooled in an ice bath as 1.0 ml. of Jones chromium trioxide reagent was added over 5 min. The solution was stirred 10 min., poured into aqueous sodium bisulfite, and extracted with benzene. The benzene solutions were washed with water, saturated aqueous sodium bicarbonate solution and brine and dried over anhydrous sodium sulfate. Solvent removal gave a colorless foam which, on crystallization from isopropyl ether, gave analytically pure (+) trans-anti-6-[(3,5-dimethyl-4-isoxazolyl)methyl]-3a-methyl-1,2,3a,4,5,9-,9a,9b-octahydro-3H-benz[e]indene-3,7(8H)-dione as white needles, m.p. 85.5°–87.5°.

Anal. Calcd. for $C_{20}H_{25}N_1O_3$: C, 73.36; H, 7.70; N, 4.28; O, 14.66. Found: C, 73.67; H, 7.95; N, 4.15.

EXAMPLE 24

Preparation of (+) 19-nor-androst-4-en-3,17-dione.

A solution of 1.308 g. of (+) trans-anti-6-[(3,5-dimethyl-4-isoxazolyl)methyl]-3a-methyl-1,2,3a,4,5,9-,9a,9b-octahydro-3H-benz[e]inden-3,7(8H)-dione, prepared as described above in Example 20, in 100 ml. of 3:1 ethanol:triethylamine containing 80 mg. of 10 per cent palladium on carbon, was hydrogenated at atmospheric pressure and room temperature. After 1½ hr., the uptake of hydrogen ceased. Filtration, followed by solvent removal, gave trans-anti-trans-6-[(3,5-dimethyl-4-isoxazolyl)methyl]-3a-methyl-3a,4,5-,5a,8,9,9a,9b-octahydro-1H-benz[e]inden-3,7(2H,6H)-dione as a colorless foam. This crude product was taken up in 10 ml. of ethylene glycol and 75 ml. of benzene and heated with 750 mg. of p-toluenesulfonic acid at reflux under nitrogen, with azeotropic removal of water, for 20 hr. The cooled solution was washed with saturated aqueous sodium bicarbonate solution and brine and dried over anhydrous sodium sulfate. Solvent removal gave trans-anti-trans-6-

[(3,5-dimethyl-4-isoxazolyl)methyl]-3,3,7,7-bis(ethylenedioxy)-3a-methyl-perhydro-1H-benz[e]indene as a pale yellow resin. A solution of the crude isoxazole diketal in 100 ml. of ethanol containing 2.5 g. of potassium hydroxide and 100 mg. of 10 per cent palladium on carbon was hydrogenated at atmospheric pressure and room temperature. The uptake of one equivalent of hydrogen took 5.0 hr. The catalyst was removed by filtration and the solvent was removed from the filtrates until a residue of approximately 5 ml. remained. To this solution of the vinylogous amide was added 150 ml. of 20 per cent aqueous potassium hydroxide. The mixture was degassed, placed under nitrogen, heated at reflux under nitrogen for 16 hr., cooled, and extracted with benzene. The benzene solutions were washed with brine and dried over anhydrous sodium sulfate. Solvent removal gave trans-anti-trans-3,3,7,7-bis-(ethylenedioxy)-3a-methyl-6-(3-oxobutyl)-perhydro-1H-benz[e]indene as a colorless resin. This material was taken up in 50 ml. of methanol, degassed and placed under nitrogen. To the solution was added 5 ml. of 4N-hydrochloric acid and the resulting solution was heated at reflux for 3.0 hr. The cooled solution was diluted with water and extracted with benzene. The benzene solutions were washed with water, saturated aqueous sodium bicarbonate solution and brine and dried over anhydrous sodium sulfate. Solvent removal gave crude 19-nor-androstene dione as a pale tan crystalline solid. Filtration of this material through silica gel with 9:1 benzene:ether followed by crystallization from acetone-hexane gave (+) 19-nor-androst-4-en-3,17-dione as shiny platelets, m.p. 173°–174°.

EXAMPLE 25

Preparation of (+) trans-anti-3a-methyl-6-(3-oxobutyl)-3a,4,5,9,9a,9b-hexahydro-1H-benz[e]inden-3,7(2H,8H)-dione.

A solution of 981 mg. of (+) trans-anti-6-[(3,5-dimethyl-4-isoxazolyl)methyl]-3a-methyl-1,2,3a,4,5,9,9a,9b-octahydro-3H-benz[e]inden-3,7-(8H)-dione, prepared as described in Example 20, and 600 mg. of p-toluenesulfonic acid in 15 ml. of ethylene glycol and 50 ml. of benzene was degassed, placed under nitrogen and heated at reflux with azeotropic removal of water, for 23 hr. The cooled solution was washed with excess saturated aqueous sodium bicarbonate solution and brine and dried over anhydrous sodium sulfate. Solvent removal gave trans-anti-6-[(3,5-dimethyl-4-isoxazolyl)methyl]-3,3,7,7-bis-(ethylenedioxy)-3a-methyl-2,3,3a,4,6,7,8,9,9a,9b-decahydro-1H-benz[e]indene as a colorless resin. This material was taken up in 60 ml. of ethanol containing 3.0 g. of potassium hydroxide and 100 mg. of 10 per cent palladium on carbon and hydrogenated at atmospheric pressure and room temperature. Uptake of one equivalent of hydrogen took 6.0 hr. The catalyst was removed by filtration and the solvent was removed from the filtrates until approximately 10 ml. remained. To this solution of vinylogous amide was added 75 ml. of 20 per cent aqueous potassium hydroxide and the resulting mixture was heated at reflux under nitrogen for 18 hours. The cooled mixture was diluted with water and extracted with benzene. The benzene solutions were washed with brine and dried over anhydrous sodium sulfate. Solvent removal gave trans-anti-3,3,7,7-bis(ethylenedioxy)-3a-methyl-6-(3-oxobutyl)-2,3,3a,4,6,7,8,9,9a,9b-decahydro-1H-benz[e]indene as a very pale yellow resin. This material was taken up in 500 ml. of 1:1 water-acetic acid, degassed, placed under nitrogen, and heated at 90°–100° for 1½ hr. The solution was cooled, diluted with water and extracted with benzene. The benzene solutions were washed with saturated aqueous sodium bicarbonate solution and brine and dried over anhydrous sodium sulfate. Solvent removal gave crude trione as a pale yellow resin. Crystallization of this material from isopropylether gave (+) trans-anti-3a-methyl-6-(3-oxobutyl)-3a,4,5,9,9a,9b-hexahydro-1H-benz[e]inden-3,7(2H,8H)-dione, m.p. 80°–81.5°.

EXAMPLE 26

Preparation of racemic 19-nor-9β,10α-androst-4-en-3,17-dione

A mixture containing 655 mg. (2.0 mM) of racemic trans-anti-6-(3,5-dimethyl-4-isoxazolylmethyl)-3a-methyl-1,2,3a,4,5,9,9a,9b-octahydro-3H-benz(e)indene-3,7(8H)-dione, 250 mg. of 7 percent Pd/BaSO$_4$, 0.5 ml. of 48 percent HBr and 20 ml. of ethanol was hydrogenated at atmospheric pressure and room temperature for a period of 8 hours. The catalyst was removed by filtration and washed with fresh ethanol. The filtrates were diluted with benzene and washed twice with brine and once each with sodium bicarbonate and brine. The organic layer was then dried over sodium sulfate and the solvent removed to give 650 mg. of a bone-white solid. This material was dissolved in approximately 3 ml. of hot benzene to which was added approximately 15 ml. of ether and the solution was cooled to 0°C. After filtration there was obtained 430 mg. (65 percent yield) of fine white needles of trans-anti-cis-anti-6-[(3,5-dimethyl-4-isoxazolyl)methyl]-3a-methyl-3a,4,5,5a,8,9,9a,9b-octahydro-1H-benz[e]inden-3,7(2H,6H)-dione. An analytical sample was prepared by dissolving a small amount of the aforesaid material in methylene chloride, filtering and removing solvent. The residue was crystallized from benzene/ether to give very tiny white needles, m.p. 196°–198.5°.

Anal. Calcd. for $C_{20}H_{27}NO_3$: C, 72.92; H, 8.26; N, 4.25. Found: C, 72.57; H, 8.26; N, 4.13.

A solution containing 658 mg. (2.0 mM) of the above retrodione, 200 mg. of p-toluenesulfonic acid hydrate, 15 ml. of ethylene glycol and 60 ml. of benzene was degassed, placed under a nitrogen atmosphere and heated at reflux with removal of water for 22 hours. The solution was cooled, diluted with benzene and extracted with saturated aqueous sodium bicarbonate solution (2×), water (2×) and brine. The organic phase was dried over sodium sulfate and the solvent removed to give a cream-white solid representing crude, racemic trans-anti-trans-cis-anti-6[3,5-dimethyl-4-isoxazolyl)-methyl]-3,3,7,7-bis(ethylenedioxy)-3a-methyl-perhydro-1H-benz[e]indene.

The above isoxazolyl diketal was suspended in 40 ml. of ethanol containing 1.5 g. of KOH. There was then added 150 mg. of a 5 percent Pd/C catalyst and the resulting mixture was hydrogenated at atmospheric pressure and room temperature for approximately 1.5 hours. The catalyst was then removed by filtration and washed with fresh ethanol. The combined filtrates were evaporated to yield a residue of about 10 ml. A total of 50 ml. of 20 percent aqueous KOH was then added to the residue and the resulting solution was degassed, placed under nitrogen and heated at reflux for 20 hours. The mixture was cooled, poured into water and extracted with benzene. The benzene extracts were washed with brine and dried over sodium sulfate. Solvent removal gave a cloudy light yellow resin comprising crude, racemic trans-anti-cis-anti-3,3,7,7-bis(ethylenedioxy)-3a-methyl-6-(3-oxobutyl)perhydro-1H-benz[e]indene.

Crude ketone material was taken up in 20 ml. of dioxane, degassed, placed under a nitrogen atmosphere and cooled in an ice bath. A total of 1.0 ml. of 25 percent HCl was then added dropwise over 2 minutes. The mixture was cooled another 5 minutes and was then allowed to stir at room temperature for 22 hours. The light yellow solution was poured into excess saturated aqueous sodium bicarbonate solution and extracted with benzene. The combined benzene solutions were washed with sodium bicarbonate, brine and then dried over sodium sulfate. Solvent removal gave 603 mg. of light orange resin which crystallized slowly. This material was chromatographed on silica gel and crystallized from approximately 10 ml. of methylenechloride/ether and cooling to −20° to give 272 mg. (50 percent yield) of small white prisms which exhibited slight melting at 141°–142°; m.p. 148°–152°. Recrystallization from approximately 5 ml. of methylene chloride/ether with cooling at −20° gave 239 mg. of small white prisms, m.p. 148.5°–152° (softening at 142°) representing pure 19-nor-9$\beta$,10$\alpha$-androst-4-en-3,17-dione.

Anal. Calcd. $C_{19}H_{24}O_2$: C, 79.37; H, 8.88. Found: C, 79.07; H, 8.88.

EXAMPLE 27

Preparation of trans-anti-cis-anti-6-[(3,5-dimethyl-4-isoxazolyl)-methyl]-3,3,7,7-bis(ethylenedioxy)-3a-methyl-perhydro-1H-benz[e]indene A mixture containing 2.4 g. (7.3 mM) of racemic trans-anti-cis-anti-6-[(3,5-dimethyl-4-isoxazolyl)methyl]-3a-methyl-3a,4,5,5a,8,9,9a,9b-octahydro-1H-benz[e]inden-3,7(2H,6H)dione, 600 mg. of p-toluenesulfonic acid hydrate, 25 ml. of ethylene glycol and 150 ml. of benzene was degassed, placed under nitrogen and heated at reflux with azeotropic removal of water for 22 hours. The resulting solution was cooled, washed with saturated aqueous sodium bicarbonate, water (2x) and brine. The organic phase was dried over sodium sulfate and the solvent removed to give 3.1 g. of a white solid. This material was dissolved in approximately 5 ml. of methylene chloride/1 percent triethylamine. To this solution was added 50 ml. of ether. After cooling to −20° there was obtained 2.805 g. of shiny pale yellow prisms, m.p. 186°–9° (fast heating). Recrystallization from 6 ml. of methylene chloride/1 percent triethylamine plus 50 ml. of ether with cooling to 0° gave 1.85 g. of colorless prisms, m.p. 188.5°–191° representing pure, racemic trans-anti-cis-anti-6-[(3,5-dimethyl-4-isoxazolyl)methyl]-3,3,7,7-bis(ethylendioxy)-3a-methyl-perhydro-1H-benz[e]indene.

Anal. Calcd. for $C_{24}H_{35}O_5N$: C, 69.03; H, 8.45; N, 3.35. Found: C, 69.14; H, 8.32; N, 3.27.

EXAMPLE 28

Preparation of (−)-19-nor-9$\beta$,10$\alpha$-androst-4-en-3,17-dione

A mixture containing 655 mg. (2.0 mM) of (+)-trans-anti-6-(3,5-dimethyl-4-isoxazolylmethyl)-3a-methyl-1,2,3a,4,5,9,9a,9b-octahydro-3H-benz[e]inden-3,7(8H)-dione, 10 percent Pd/BaSO$_4$, 1.0 ml. of 47 percent HBr and 40 ml. of ethanol was hydrogenated at atmospheric pressure and room temperature for about 5 ½ hours. The catalyst was removed by filtration and washed with fresh ethanol. The combined filtrate was eluted with benzene, washed with water, brine, saturated aqueous sodium bicarbonate solution and then with brine. The organic layers were dried over sodium sulfate and the solvent removed to yield a pale yellow resin which crystallized upon standing. After chromatography on silica gel the product was dissolved in 2 ml. of methylenechloride and 20 ml. of ether was added. After seeding and cooling to −20° there was obtained 295 mg. (45 percent yield) of fine white needles, m.p. 169°–172.5° with some previous slight softening. An analytical sample of pure (+)-trans-anti-cis-anti-6-[(3,5-dimethyl-4-isoxazolyl)methyl]-3a-methyl-3a,4,5,5a,8,9,9a,9b-octahydro-1H-benz[e]inden-3,7(2H,6H)-dione was obtained by recrystallization from methylene chloride/ether with cooling to 0°, m.p. 170.5°–174°.

Anal. Calcd. for $C_{20}H_{27}O_3N$: C, 72,92; H, 8.26; N, 4.25. Found: C, 72.80; H, 8.40; N, 4.14. $[\alpha]_D^{25}$ = +122.9° (c = 0.895, CHCl$_3$) U.V. = $\lambda_{max}$ = 222 m$\mu$ ($\epsilon$ = 4,750).

A solution containing 1.730 g. (5.25 mM) of the above dione and 400 mg. of p-toluenesulfonic acid hydrate in 25 ml. of ethylene glycol and 100 ml. of benzene was degassed, placed under nitrogen and heated at reflux with azeotropic removal of water for 22 hours. The cooled solution was washed with saturated aqueous sodium bicarbonate (2×), water (2×) and brine. The organic phase was dried over sodium sulfate and the solvent removed after filtration to give a pale yellow resin as a residue. The resin comprising (−)-trans-anti-cis-anti-6-[(3,5-dimethyl-4-isoxazolyl)-methyl]-3,3,7,7-bis(ethylenedioxy)-3a-methyl-perhydro-1H-benz[e]-indene was dissolved in 80 ml. of ethanol containing 3.5 g. of KOH and there was then added to this solution a total of 400 mg. of 5 percent Pd/C catalyst. The resulting mixture was hydrogenated at atmospheric pressure and room temperature. Uptake of hydrogen ceased after about 1½ hours. The catalyst was removed by filtration and washed with fresh ethanol. The combined ethanol filtrates were stripped of solvent until a residue of approximatley 25 ml. remained.

To this solution of vinylogous amide was added 80 ml. of 20 percent aqueous KOH and the resulting mixture was degassed placed under nitrogen and heated at reflux for 12 hours. The cooled solution was poured into water and extracted with benzene. The combined benzene extracts were washed with water and brine. The organic phase was dried over sodium sulfate and the solvent removed to give crude keto diketal as a yellow resin. The material was taken up in 50 ml. of dioxane, degassed and placed under nitrogen. The solvent was cooled in an ice bath and when the solvent began to solidify a total of 3.0 ml. of 25 per cent HCl was added dropwise over three minutes. The mixture was stirred at 0° for an additional 10 minutes and then at room temperature for 22 hours. The mixture was then diluted with benzene and then washed with water, brine, saturated aqueous sodium bicarbonate and then brine again. The organic phase was dried over sodium sulfate and the solvent removed to yield a yellow resin. The crude steroid was purified by chromatography over silica gel followed by crystallization from acetone/isopropyl ether 1:10 with cooling to −20° to yield (−)-19-nor-9β,10α-androst-4-en-3,17-dione as white needles, m.p. 131°–135.5°. Recrystallization from acetone/isopropyl ether as above gave white needles of pure product, m.p. 132°–135.5°.

Anal. Calcd. for $C_{18}H_{24}O_2$: C, 79.37; H, 8.88 Found: C, 79.24; H, 8.87. $[\alpha]_D^{25} = -23.9°$ (c = 1.055, $CHCl_3$) U.V. $\lambda_{max} = 239-240$ mμ (ε = 17,300).

EXAMPLE 29

Preparation of
(−)-trans-anti-cis-anti-6-[(3,5-dimethyl-4-isoxazolyl)-methyl]-3,3,7,7-bis(ethylene dioxy)-3a-methyl-perhydro-1H-benz[e]indene A mixture containing 1.76 g. (5.33 mM) of (+)-trans-anti-cis-anti-6-[(3,5-dimethyl-4-isoxazolyl)-methyl]-3a-methyl-3a,4,5,5a,8,9,9a,9b-octahydro-1H-benz[e]inden-3,7(2H,6H)-dione, 400 mg. of p-toluenesulfonic acid hydrate, 15 ml. of ethylene glycol and 100 ml. of benzene was degassed, placed under nitrogen and heated at reflux with azeotropic removal of water for 22 hours. The cooled solution was washed with saturated aqueous sodium bicarbonate (2×), water (2×) and brine. The organic phase was dried over sodium sulfate and then the solvents removed to give 2.34 g. of a colorless glass which soon crystallized. Crystallization from acetone/isopropyl ether after cooling to −20° gave 2.03 g. of white needles, m.p. 155°–158°. Recrystallization from methylene chloride/isopropyl ether with cooling to −20° gave 1.775 g. of fine white needles, m.p. 156°–158.5° of the above-captioned product.

Anal. Calcd. for $C_{24}H_{35}NO_5$: C, 69.03; H, 8.45; N, 3.35. Found: C, 68.93; H, 8.47; N, 3.36. $[\alpha]_D^{25} = 31.6°$ (c = 0.87 $CHCl_3$) U.V. $\lambda_{max} = 223-224$ mμ (ε = 4,900).

EXAMPLE 30

Preparation of racemic
19-nor-9β,10α-androst-4-en-3,17-dione via tricyclic triketone A suspension containing 725 mg. (1.92 mM) of trans-anti-cis-anti-3,3,7,7-bis(ethylenedioxy)-3a-methyl-6-(3-oxobutyl)-perhydro-1H-benz[e]indene in 30 ml. of 1:1 acetic acid/water was degassed, placed under nitrogen and heated at 95° for 1 ½ hour. The cooled mixture was poured into water and the resulting mixture was extracted with benzene. The combined benzene extracts were washed with brine, saturated sodium bicarbonate solution and brine again. The organic phase was dried over sodium sulfate and after removal of the solvent there was obtained a pale yellow resin comprising crude racemic, trans-anti-cis-anti-3a-methyl-6-(3-oxobutyl)-perhydro-1H-benz[e]inden-3,7-dione. This material as taken up in 25 ml. of 2-methoxyethanol and 1.01 ml. of pyrrolidine was added. The mixture was degassed, placed under nitrogen and heated at 95°–100° for 16 hours. A total of 10 ml. of acetate buffer was added and heating was continued for an additional 2 hours. The mixture was poured into water and extracted with benzene. The benzene solutions were washed with brine, saturated aqueous bicarbonate and brine and dried over sodium sulfate. Removal of the solvents gave a light brown resin which crystalized on standing. This resin was chromatographed on silica gel using benzene/ether 8:2 as eluent yielded the above-captioned product as light orange crystals. Recrystallization from methylene chloride/ether with cooling to −20° yielded light yellow prisms, m.p. 147°–151° (softening at 138°).

EXAMPLE 31

Preparation of racemic
13-ethyl-9β,10α-gon-4-en-3,17-dione

A mixture containing 1.032 g. (3.0 mM) of racemic trans-anti-3a-ethyl-1,2,3a,4,5,9,9a,9b-octahydro-3H-benz[e]inden-3,7(8H)-dione (prepared in analogous fashion to that described in Examples 8 and 9 with the exception that 2-ethylcyclopentane-1,3-dione was employed instead of the corresponding methyl compound), 300 mg. of 10 percent Pd/BaSO₄ and 60 ml. of ethanol was stirred at room temperature for 50 minutes. A total of 1.5 ml. of 45 percent HBr was then added and the resulting mixture was hydrogenated at atmospheric pressure and room temperature for a period of about 6 ½ hours at which time uptake of hydrogen ceased. The catalyst was removed by filtration and washed with fresh ethanol. The combined ethanol filtrates were diluted with benzene, washed with water and brine, saturated aqueous sodium bicarbonate solution and then with brine again. The organic phase was dried over sodium sulfate and the solvent removed to give 1.043 g. of a white solid. This material was chromatographed on silica gel first using benzene/ether at 8:2 and finally at 7:3. The latter eluates were combined and evaporated to give 956 mg. of a white slid which on crystallization from methylene chloride/ether 1:10 and cooling to −20° gave 781 mg. of fine white needles, m.p. 174°–176.5° (sint. 160°–162°). Recrystallization with the same procedure gave 752 mg. (72 percent yield) of pure, racemic trans-anti-cis-anti-6-[(3,5-dimethyl-4-isoxazolyl)methyl]-3-a-ethyl-3a,4,5,5a,8,9-,9a,9b-octahydro-1H-benz[e]inden-3,7(2H,6H)-dione.

A solution containing 2.748 (8.0 mM) of the above isoxazolyl dione and 600 mg. of p-toluenesulfonic acid hydrate in 25 ml. of ethylene glycol and 100 ml. of benzene was degassed, placed under nitrogen and heated at reflux with azeotropic removal of water for 22 hours. The mixture was cooled, washed with saturated aqueous sodium bicarbonate (2×), water (2×), and brine. The organic phase was dried over sodium sulfate and the solvents removed to yield a white crystaline solid comprising racemic trans-anti-cis-anti-6-[(3,5-dimethyl-4-isoxazolyl)methyl]-3,3,7,7-bis(ethylenedioxy)-3a-ethyl-perhydro-1H-benz[e]indene.

The above crude ketal was suspended in a solution containing 5 g of sodium hydroxide in 125 ml. of ethanol and 650 mg. of 5 percent Pd/C was added. The resulting mixture was hydrogenated at atmospheric pressure and room temperature. After 4½ hours the uptake of hydrogen had ceased. The catalyst was removed by filtration and washed with fresh ethanol. The solvent was removed until a residue of approximately 50 ml. remained. To this solution was added 100 ml. of 20 percent aqueous sodium hydroxide and the resulting mixture was degassed, placed under nitrogen and heated at reflux for 16 hours. The resulting mixture was poured into water and extracted with benzene. The benzene solutions were washed with water, brine and then dried over sodium sulfate. Removal of the solvent gave a yellow resin. This material was taken up in 100 ml. of methanol and 10 ml. of 3N HCl was added. This mixture was degassed, placed under nitrogen and heated at reflux for 4 hours. The mixture was diluted with benzene, washed with water (2×), saturated sodium bicarbonate and brine. The organic phase was dried over sodium sulfate and the solvent removed to give a yellow oily solid.

Chromatography of the above crude retrosteroid on silica gel followed by crystallization from 25 ml. of acetone with cooling to −20° gave 1.494 g. of cream-white prisms, m.p. 197°–206.5°. Recrystallization from 25 ml. of acetone with cooling to −20°, gave 1.349 (59 percent yield) of small, colorless prisms m.p. 203°–207.5°. An analytical sample of the product 13-ethyl-9β,10α-gon-4-en-3,17-dione was obtained by a further crystallization from acetone as before to yield a material melting at 203.5°–207°.

Anal. Calcd. for $C_{19}H_{26}O_2$: C, 79.68; H, 9.15. Found: C, 79.69; H, 9.12. U.V. - $\lambda_{max} = 240$ m$\mu$ ($\epsilon = 17,900$).

EXAMPLE 32

Preparation of racemic trans-anti-cis-anti-6-[(3,5-dimethyl-4-isoxazolyl)methyl]-3,3,7,7-bis(ethylenedioxy)-3a-ethyl-perhydro-1H-benz[e]indene A total of 1.71 g. (5.0 mM) of racemic trans-anti-cis-anti-6-[(3,5-dimethyl-4-isoxazolyl)methyl]-3a-ethyl-3a,4,5,5a,8,9,9a,9b-octahydro-1H-benz[e]inden-3,7(2H,6H)-dione, 0.5 g. of p-toluenesulfonic acid hydrate, 20 ml. of ethyleneglycol and 100 ml. of benzene was degassed, placed under nitrogen and heated at reflux with azeotropic removal of water for 21 hours. The mixture was cooled, washed with sodium bicarbonate solution (2×), water (2×) and brine. The organic phase was dried over sodium sulfae and the solvent removed to give a white solid. Crystallization from approximately 25 ml. of methylene chloride/ether with cooling to −20° gave 1.836 g. of small white prisms melting at 181°–185°. Recrystallization from approximately 10 ml. of the same solvent with cooling to 0° gave 1.49 g. of small white prisms, melting at 183°–186.5° of the above-captioned product.

Anal. Calcd. for $C_{25}H_{37}O_5N$: C, 69.57; H, 8.64; N, 3.25. Found: C, 69.55; H, 8.69; N, 3.20.

We claim:
1. A compound of the formula

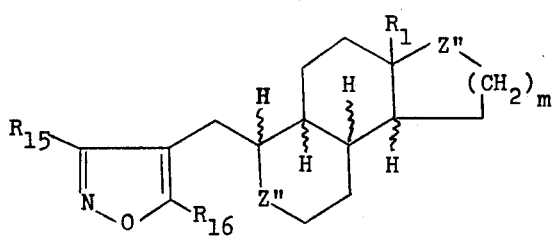

wherein Z″ is selected from the group consisting of lower-alkylenedioxy-methylene, di-lower alkoxy-methylene, phendioxy-methylene and a group of the formula

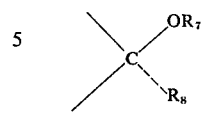

wherein $R_7$ is selected from the group consisting of hydrogen, lower alkyl, lower alkoxy-lower alkyl, tetrahydropyranyl, lower alkanoyl and benzoyl; $R_8$ is selected from the group consisting of hydrogen and lower aliphatic hydrocarbyl; $R_1$ is a primary alkyl group of from 1 to 5 carbons; m is an integer having a value of 1 or 2; $R_{15}$ is selected from the group consisting of lower alkyl and hydrogen; $R_{16}$ is selected from the group consisting of lower alkyl, lower alkylphenyl, phenyl lower alkyl and hydrogen.

2. The compound as in claim 1 wherein m is 1; $R_1$ is methyl or ethyl; $R_{15}$ and $R_{16}$ are each independently lower alkyl; Z″ is lower alkylenedioxy-methylene or a group of the formula

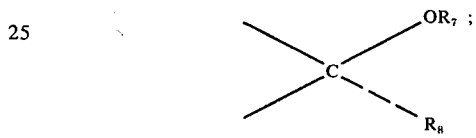

$R_8$ is hydrogen; $R_7$ is lower alkyl, lower alkanoyl, benzoyl or hydrogen: and the configuration is trans-anti-trans.

3. The compound as in claim 2 wherein m is 1; $R_1$ is methyl or ethyl; $R_{15}$ and $R_{16}$ are each independently lower alkyl; Z″ is lower alkylenedioxy-methylene or a group of the formula

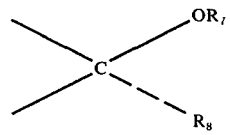

$R_8$ is hydrogen; $R_7$ is lower alkyl, lower alkanoyl, benzoyl or hydrogen; and the configuration is trans-anti-cis.

4. A compound as in claim 2 which is trans-anti-trans-6-[(3,5-dimethyl-4-isoxazolyl)-methyl]-3,3,7,7-bis(ethylenedioxy)-3a-methyl-perhydro-1H-benz[e]indene.

5. A compound as in claim 3 which is trans-anti-cis-6-[(3,5-dimethyl-4-isoxazolyl)-methyl]-3,3,7,7-bis(ethylenedioxy)-3a-methyl-perhydro-1H-benz[e]indene.

6. A compound as in claim 3 which is trans-anti-cis-6-[(3,5-dimethyl-4-isoxazolyl)-methyl]-3,3,7,7-bis(ethylenedioxy)-3a-ethyl-perhydro-1H-benz[e]indene.

* * * * *